(12) United States Patent
Osborne et al.

(10) Patent No.: US 8,361,797 B2
(45) Date of Patent: Jan. 29, 2013

(54) MYELOMA CELL CULTURE IN TRANSFERRIN-FREE LOW IRON MEDIUM

(75) Inventors: Matthew David Osborne, Kent (GB); Jonathan H. Dempsey, Cambridge (GB)

(73) Assignee: Medimmune Limited, Cambridge (GB)

( * ) Notice: Subject to any disclaimer, the term of this patent is extended or adjusted under 35 U.S.C. 154(b) by 733 days.

(21) Appl. No.: 10/567,453

(22) PCT Filed: Jul. 28, 2004

(86) PCT No.: PCT/GB2004/003273
§ 371 (c)(1), (2), (4) Date: Jul. 18, 2006

(87) PCT Pub. No.: WO2005/014800
PCT Pub. Date: Feb. 17, 2005

(65) Prior Publication Data
US 2007/0031964 A1    Feb. 8, 2007

Related U.S. Application Data

(60) Provisional application No. 60/493,450, filed on Aug. 8, 2003.

(30) Foreign Application Priority Data

Aug. 8, 2003 (GB) .................................. 0318679.8

(51) Int. Cl.
*C12N 15/00* (2006.01)
*C12N 15/06* (2006.01)
*C12N 15/78* (2006.01)

(52) U.S. Cl. ...................... 435/455; 435/325; 435/372.1; 435/383; 435/404

(58) Field of Classification Search ........................ None
See application file for complete search history.

(56) References Cited

U.S. PATENT DOCUMENTS

| 5,316,938 | A | * | 5/1994 | Keen et al. | ..................... 435/404 |
| 5,573,937 | A |   | 11/1996 | Shinmoto et al. | |
| 6,593,140 | B1 | * | 7/2003 | Field | ............................. 435/404 |
| 2005/0069979 | A1 | * | 3/2005 | Zeng et al. | .................... 435/69.1 |
| 2006/0148074 | A1 | * | 7/2006 | Gorfien et al. | ................ 435/325 |

FOREIGN PATENT DOCUMENTS

| GB | 2 196 348 | 4/1988 |
| WO | 92/05246 | 4/1992 |
| WO | 93/00423 | 1/1993 |
| WO | 94/02592 | 2/1994 |

OTHER PUBLICATIONS

Keen et al, "Adaptation of cholesterol-requiring NS0 mouse myeloma cells to high density growth in a fully defined protein-free and cholesterol-free culture medium", Cytotechnology 17:203-211, 1995.
Kovar et al., "Iron compounds at high concentrations enable hybridoma growth in a protein-free medium", Biotechnology Letters, vol. 9, No. 4, 1987, pp. 259-264, XP009037179.
Neumannova et al., "Growth of human tumor cell lines in transferring-free, low-iron medium", in vitro cellular & developmental biology—Animal, vol. 31, No. 8, Sep. 1995, pp. 625-632, XP001118629.
M.J. Keen, "The culture of rat myeloma and rat hybridoma cells in a protein-free medium", Cytotechnology, vol. 17, No. 3, 1995, pp. 193-202, XP009037173.
Dempsey et al., "Improved fermentation processes for NSO cell lines expressing human antibodies and glutamine synthetase", Biotechnology Progress, vol. 19, No. 1, Jan. 2003, pp. 175-178, XP002298041.
Rasmussen et al, "Phosphate compounds as iron chelators in animal cell cultures", in Vitro Cell Dev Biol. Apr. 1986; 22(4):177-9.
Bibila et al, "In Pursuit of the Optimal Fed-Batch Process for Monoclonal Antibody Production", Biotechnol. Prog. 1995, 11, 1-13.

* cited by examiner

Primary Examiner — Maria Marvich
(74) Attorney, Agent, or Firm — Nixon & Vanderhye P.C.

(57) ABSTRACT

The present invention relates to a method for culturing mammalian cells in a culture medium which is transferrin free and which contains no lipophilic or synthetic nitrogen-containing chelators. Also provided is the use of the medium and a process for providing a mammalian product by culturing cells capable of producing the product in the medium.

17 Claims, 14 Drawing Sheets

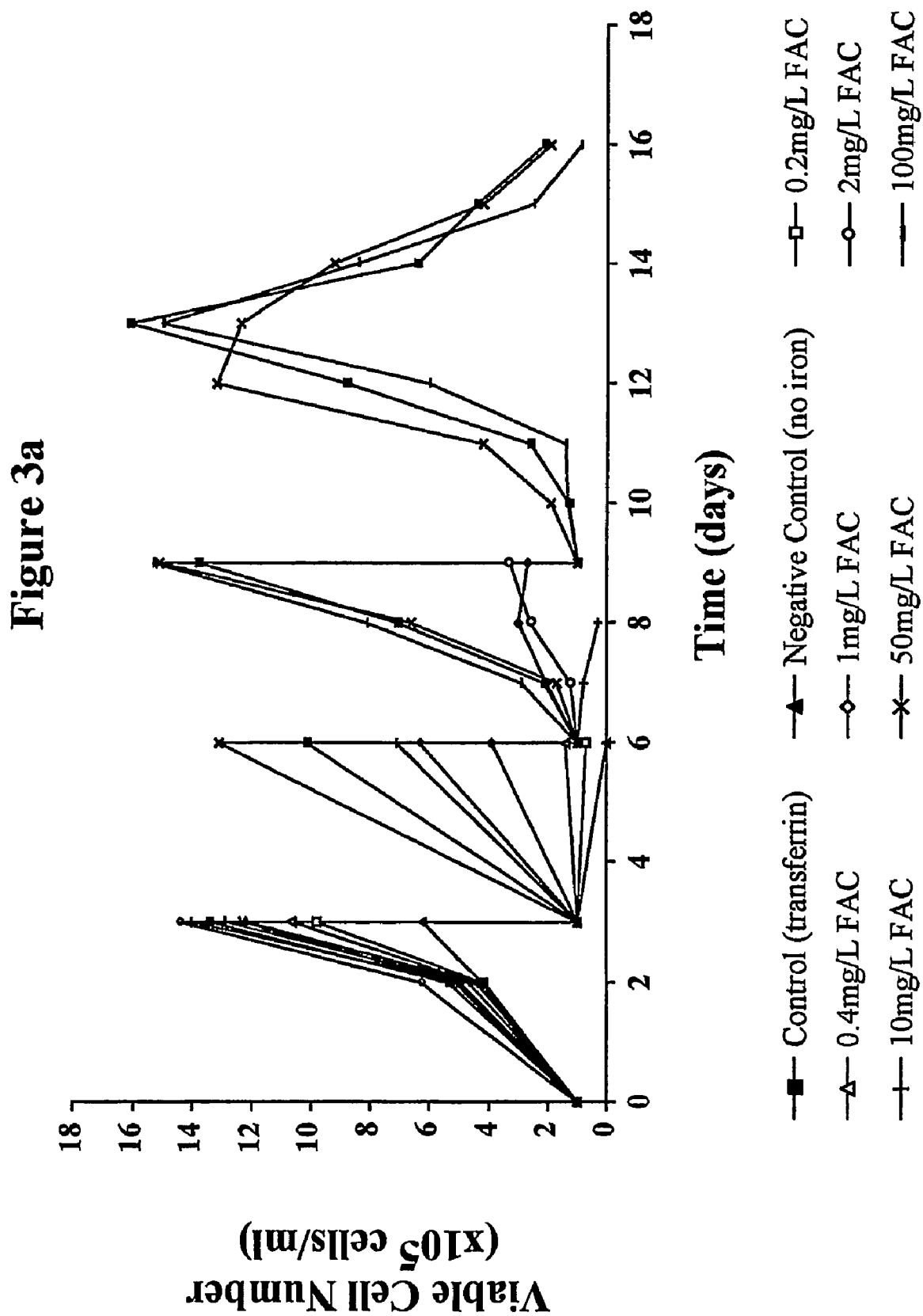

MYELOMA CELL CULTURE IN TRANSFERRIN-FREE LOW IRON MEDIUM

This application is the US national phase of international application PCT/GB2004/003273, filed 28 Jul. 2004, which designated the U.S. and claims benefit of U.S. Provisional No. 60/493,450, filed 8 Aug. 2003, and claims priority of GB 0318679.8, filed 8 Aug. 2003, the entire contents of each of which are hereby incorporated by reference.

The present invention relates to a method for growing certain mammalian cells in a culture medium containing iron but in the absence of transferrin or a lipophilic or synthetic nitrogen-containing chelator.

BACKGROUND

Cell culture media must provide the nutrients necessary to maintain and grow cells in a controlled, artificial and in vitro environment. The particular characteristics of the cell culture media depend to a large extent on the type of cell being cultured and, to a lesser extent on the method of culture.

Mammalian cells have an absolute requirement for iron, which, in vitro, is supplied in the cell culture medium. Bertheussen (Cytotechnology 11:219-231, 1993) has commented that iron cannot be effectively supplied to mammalian cells by adding simple iron salts to the cell culture medium, primarily due to the availability of iron to the cells being reduced by rapid oxidation and precipitation of iron.

Iron in free form, furthermore, has a high oxidative potential, which may result in oxidation of components of a cell culture medium. It has therefore been proven to be of benefit to complex the iron so as to reduce or eliminate this oxidative potential.

In vivo, iron is presented to the mammalian cells by the iron binding protein transferrin. Transferrin works by binding iron and interacting with a transferrin receptor on the cell surface. The transferrin-iron complex is then taken into the cell by endocytosis. Once in the cell, the transferrin-iron complex is broken and the released iron is then complexed to an iron transporting protein (ferritin). The transferrin is recycled. Thorstensen and Romslo, Biochem. J., 271:1-10 (1990) offer an excellent review of this in vivo iron transfer mechanism. The ability of transferrin to mediate transport of iron to cells has been exploited in cell culture by the simple addition of transferrin and an iron salt to the cell culture medium.

However, the transferrin typically used in cell culture media is of animal origin and in recent years there has been increasing regulatory pressure to remove proteins of animal origin from cell culture processes. Clearly the use of proteins of animal origin carries with it the risk of introducing contaminants and adventitious pathogens such as Creutzfeld-Jakob disease (CJD) or Spongiform Encephalopathy (Mad Cow Disease). Alternative iron transporters to transferrin have therefore been sought and applied with varying degrees of success. The type and concentration of any alternative iron transporter has often been found to be dependent on the type of mammalian cell being cultured.

Kovar and Franek (Biotechnology Letters 9:259-264 (1987)) demonstrated that various soluble iron compounds, such as ferric citrate, could be used in place of transferrin in the culture of hybridoma cell lines. Kovar and Franek tested the ability of ferric citrate to support the growth of two hybridoma cell lines over a concentration range of 5 µM (1.25 mg/L) to 5 mM (1225 mg/L). Although lower concentrations of ferric compounds had been proposed in earlier prior art to be suitable for use in culture media for several different cell lines (in particular those of human leukaemic or epithelial origin), Kovar and Franek report that if ferric citrate was to support hybridoma cell growth with equivalence to transferrin, it was required at a concentration of 500 µM (122.5 mg/L). Kovar and Franek found that the medium containing 500 µM ferric citrate was suitable for the culture of other hybridoma cell lines and was also suitable for the culture of several myeloma cell types.

Eto, et al., (Agric. Biol. Chem. 55(3):863-865 (1991)), report similar findings to Kovar and Franek. These workers tested the growth stimulating effect of ferric citrate over a concentration range of 10 mg/L to 600 mg/L on a hybridoma cell line. They report that 300 mg/L was used for further studies. Growth equivalent to that achieved with transferrin was observed when ethanolamine (a lipid precursor) was added at a concentration of 10 µM to the medium containing 300 mg/L ferric citrate.

In a similar study, Toyoda & Inouye, (Agric. Biol. Chem. 55(6):1631-1633 (1991)), tested the growth of three hybridoma cell lines in media containing ferric citrate over a concentration range of 0 to 500 µM. They report that for two of the three hybridoma cell lines tested, 50 µM (12.5 mg/L) ferric citrate was found to be optimal. This result is contrary to the findings of Eto et al., and Kovar and Franek, although a concentration of 500 µM was found optimal for the third cell line.

It is, however, important to note that the work of Kovar & Franek, Toyoda & Inouye, and Eto et al. was all carried out in static culture. WO 94/02592 reports that although 10 mg/L ferric ammonium citrate (FAC) was able to support hybridoma growth in static culture, this was not the case in agitated suspension culture. It is apparent, therefore, that the ability of hybridoma cells to make optimal use of the iron when grown in agitated suspension culture is different from that in static culture.

WO 93/00423 describes a culture medium additive comprising an iron chelate of a soluble iron salt and an alkali metal or alkaline earth metal citrate which is a suitable iron source for serum-free of protein-free culture media. The Examples of this application are concerned predominantly with the growth of mammalian cells such as BHK and CHO cells. Although Example 5 purports to demonstrate the growth of myeloma cells, it is noted that the SP2/0 cells used are in fact non-secreting mouse/mouse hybridoma cells. Culture conditions are specified throughout as being static suspension culture.

Kovar and Franek claim that their medium containing 500 µM ferric citrate was suitable for agitated suspension culture but show no evidence to support this claim. Qi et al., (Cytotechnology 21:95-109 (1996)), however, report that a medium containing 500 µM (122.5 mg/L) ferric citrate, as described by Kovar and Franek, was suitable for the culture of three hybridoma cell lines in agitated suspension cultures. However, Qi et al. found that in order to use a medium containing these high concentrations of ferric citrate (500 µM), it was necessary to wean the cells onto this medium; in the case of one cell line this weaning period was highly protracted. Qi et al. comment that under these conditions the cells were experiencing difficulty adapting and that the medium formulation could be improved by substitution of the ferric citrate in the medium with a more efficient iron presenting compound such as aurin tricarboxlic acid.

In agreement with the prior art cited by Kovar and Franek (1987), several workers have reported that certain types of mammalian cell have been found to be sustainable in culture using lower concentrations of iron compounds.

Ramos et al., WO 92/05246, reports that in the cultivation of epithelial cell lines and in particular Chinese Hamster Ovary (CHO) cell lines, transferrin can be replaced with ferric citrate at 10-100 mg/L (providing approximately 0.6-16 mg/L iron). However, this patent application states clearly that the medium was found not to be suitable for the culture of myeloma cell lines. Keen et al., U.S. Pat. No. 5,633,162, report that ferric citrate, ferrous sulphate and ferric ammonium citrate (FAC) can be used at concentrations of between 0.25 and 5 mg/L (equivalent to 0.04 to 0.8 mg/L iron) to replace transferrin in the culture of CHO cells. WO 98/08934 defines a replacement medium in which all animal proteins, i.e. transferrin and insulin, have been replaced. Transferrin was replaced by ferrous sulphate chelated to a nitrogen-containing chelating compound at concentrations, based on iron, of between 0.28 and 11 mg/L, with 1.1 mg/L being found to be optimal. The nitrogen containing chelating compounds stated as suitable include: ethylenediaminetetraacetic acid (EDTA); ethyleneglycol-bis(β-aminoethyl ether)-N,N,N',N'-tetraacetic acid (EGTA); desferoxamine mesylate; diethylenetriaminepentaacetic acid (DTPA) and trans-1,2-diaminocyclohexane-N,N,N',N'-tetraacetic acid (CDTA). Of these, EDTA is the most preferred. Ferric citrate was also used in the form of $FeCl_3$-sodium citrate, but this was required at higher concentrations than the ferrous sulphate.$7H_2O$-EDTA chelate.

This application states that the transferrin free medium is suitable for growing mammalian cells, particularly epithelial or fibroblast cells. Exemplification of the growth of CHO and the human embryonic kidney cell line 293 has been provided.

A range of cell types were also tested by Neumannova et al., (In vitro Cell Dev. Biol., 31:625-632 (1995)) for long term growth in media containing iron in the form of ferric citrate at the low concentration of 1.25 mg/L (approximately 0.2 mg/L iron). Of the 19 cell lines tested only 5 were capable of long term growth in this low iron medium. The 5 cell lines were Jurkat, J111 and THP-1 (human leukaemia cell lines), HeLa (a human epithelial cell line) and XC (a rat sarcoma). Although hybridoma and myeloma cell lines were included amongst those tested, none was found to be able to grow in the low iron medium.

As discussed above, lower concentrations of ferric compounds are suitable for use in culture media for certain cell types (particularly those of epithelial and human leukaemic origin). It is, however, generally agreed In the art that, in order to cultivate hybridoma cells in agitated suspension culture using a transferrin free medium, a high concentration, for example in the region of 122.5 mg/L, of an iron compound is required.

The prior art also teaches, however, that high concentrations of iron are not advantageous. Bertheussen, in Cytotechnology 11:219-231(1993), states that high concentrations of iron, such as the 500 μM ferric citrate suggested by Kovar and Franek, should not be used as these high concentrations cause rapid precipitation of iron hydroxide in the medium. Freshly formed iron hydroxide absorbs other metals and various organic molecules efficiently, thus the composition and stability of media containing high iron will be seriously affected.

In view of the difficulties encountered in delivering iron to certain mammalian cells in culture, in particular to hybridoma cells, the concept of chelation of the iron, e.g. to lipophilic compounds was developed.

Iron chelators are typically heterocyclic compounds which attach the metal ion by co-ordinate bonds to at least two non-metal ions in the chelator, and they can be classified using a number of criteria such as their origin (synthetic or biologically produced molecules), their interaction with solvents such as water (hydrophobic vs hydrophilic) or their stochiometric interaction (bidentate of hexadentate).

Lipophilic chelators are compounds which have two distinct properties: (1) the compounds are hydrophobic and often aromatic, thus exhibiting solubility in organic solvents (e.g. alcohol) but limited solubility in water; (2) the compounds also, typically, have a region of negative charge which allows "binding" of iron through electrostatic interactions with positively charged iron ions. In cell culture, it is thought that such compounds will be attracted to the lipid rich membranes of the cells and will, therefore, transport "bound" iron to and possibly through the cell membrane, thus facilitating the supply of iron to the cells (U.S. Pat. No. 5,045,468). The lipophilic chelators are typically added in excess of an accompanying iron salt.

One of the earliest reports of the use of a lipophilic chelator was by Brock and Stevensen (Immunology Letters 15:23-25, (1987)) who used pyridoxal isonicotinoyl hydrazone (PIH) in conduction with ferric nitrilotriacetate. They found that PIH: ferric nitrilotriacetate at a ratio of 2:1 and a concentration of 40 μM (based on PIH) could replace transferrin for the culture of mouse lymphocyte cell lines.

Darfler, (U.S. Pat. No. 5,045,468/in Vitro Cell. Dev. Biol. 26:769-778, 1990) reports a protein free medium suitable for the culture of hybridoma cell lines. The author found that transferrin could be replaced by using the organo iron compound, sodium nitroprusside (SNP) together with EDTA at concentrations of 5.7 and 5.5 mg/L respectively. The author named this medium "ABC medium".

Bertheussen, (U.S. Pat. No. 5,045,467/Cytotechnology 11:219-231 (1993)), reported that the transferrin in cell culture media could be replaced by using aurin tricarboxlic acid, a lipophilic iron chelator, and 3 μM ferric ions (added in the form of $FeCl_3$). Bertheussen developed this medium using several cell types and found it especially suitable for the culture of fast growing hybridoma cell lines.

WO 94/02592 proposed that tropolone be used to replace the function of transferrin in the presentation of iron to cells in agitated suspension culture. The author comments that tropolone should be added in excess of accompanying iron. The iron may be presented as ferric or ferrous ions using a variety of iron compounds, with FAC the most preferred. A hybridoma cell line was used to elucidate the optimum concentrations of tropolone and FAC as 5 μM and 0.2 mg/L respectively. This medium was also suitable for the growth of NSO myeloma cells. Purely as experimental controls, media lacking transferrin and tropolone but containing FAC were tested with hybridoma and myeloma cells. It was found that FAC alone, between 0.1 and 10 mg/L, was incapable of supporting the growth of hybridoma cells in agitated suspension culture. FAC alone at a concentration of 0.2 mg/L could not support the growth of the NSO myeloma cell lines. No other concentrations of FAC alone were investigated with the myeloma cell lines: presumably the authors assumed that NSO and hybridoma cell lines behave similarly and did not expect other concentrations of FAC to support cell growth.

Keen (Cytotechnology 17:193-202, 1995) reports the development of a protein free medium for the culture of rat myeloma and rat hybridoma cells. This medium, called W38, was based on a 1:1:1 mixture of DMEM, RPMI and the ABC medium developed by Darfler. The medium therefore contained SNP as a lipophilic source of iron and EDTA as a nitrogen containing chelator. SNP and EDTA were, however, at ⅓ of the concentration found in the ABC medium, and Keen found it beneficial to increase the iron concentration by including ferric citrate in the medium. W38 medium was also suitable for the cultivation of the cholesterol auxotrophic myeloma cell line, NS0, providing suitable provision for the cholesterol requirement was made (Keen and Steward, Cytotechnology 17:203-211, 1995).

A recent patent application by Epstein et al., WO 01/16294, comments that in many cases simple iron carriers such as citrate do not provide sufficient iron availability to, or uptake by, cultured cells. The patent also reports that a range of lipophilic iron chelating compounds could be used for a variety of cell types with differing degrees of success. However, results at least as good as transferrin were only obtained with sorbitol chelated to $FeCl_3$ and 2-hydroxypyridine-N-oxide.

The use of lipophilic compounds to chelate and aid presentation of iron in transferrin free culture of hybridoma and myeloma cell types has therefore become state of the art. There are, however, several disadvantages to the inclusion of lipophilic chelators in cell culture medium. The lipophilic chelators are often toxic, for example SNP is classified as highly toxic and has an LD50 in rat of <1 mg/kg. In cell lines used for the industrial production of biotherapeutic products, this has consequences for both manufacturing operators and the final product. Indeed, it may be necessary to develop and validate assays to prove that the final purified biotherapeutic product is clear of any contaminating lipophilic chelator. Additionally, optimisation of the iron concentration of any particular process will be further complicated due to the two-component system of chelator and iron compound.

In summary, the prior art shows that:
1. in the absence of transferrin, hybridoma and myeloma cells will grow in high iron concentrations (122.5 mg/L ferric citrate) (Kovar & Franek).
2. high iron concentrations (e.g. 122.5 mg/L ferric citrate) cause precipitation which damages the culture medium (Bertheussen).
3. in the absence of transferrin or a lipophilic chelator, hybridoma cells will not grow in agitated culture and myeloma cells will not grow at all in low iron concentrations (0.1-10 mg/L and 0.2 mg/L respectively) (WO 94/02592).
4. a lipophilic chelator is required in the medium to enable hybridoma and myeloma cells to grow in agitated culture in low iron concentrations (WO 94/02592).
5. low iron concentrations can be used for growth of certain mammalian cells, but only with the use of a nitrogen-containing chelator such as EDTA (WO 98/08934).

Within the art of cell culture It is appreciated that certain cell types share similar nutritional attributes. It is notable that both myeloma and hybridoma cell types share significant attributes that are not always exhibited by other cell types, for example glutamine auxotrophy (Bebbington et al. Biotechnology 10:169-175, 1992). The fact that hybridomas and myelomas react in a similar way in many respects is, to a certain extent, unsurprising since hydridoma cell lines are produced by fusion of a myeloma cell with an antibody producing B lymphocyte (Kohler and Milstein, Nature 256:495-497, 1975).

The prior art, as outlined above, has shown that the ability of hybridoma and myeloma cells to use iron present in the medium with a simple iron carrier, such as a citrate, and in the absence of transferrin or a lipophilic or nitrogen-containing chelator is different from the corresponding ability of, for example, CHO cells. The overall teaching of the prior art is that hybridoma and myeloma cells are the same in their ability to use iron in a transferrin-free culture medium.

It is apparent from the literature, as discussed above, that time and effort have been dedicated to the development of transferrin free media for the growth of hybridoma cell types, particularly in static culture. On the art-implied assumption that myeloma cells will demonstrate the same requirements as hybridoma cells in this respect, an equivalent effort has not been made with myeloma cells.

Over the years, it is apparent that the art of hybridoma and myeloma cell culture has moved away from the use of iron in the form of a soluble iron compound as a replacement for transferrin, and instead has determined that to reap the benefits of low iron concentrations, a lipophilic or nitrogen-containing chelator must be included in a culture medium. Of course the use of such chelators in media used to grow cells for the product they have been engineered to produce, also necessitates that the product is further treated to ensure there is no contamination with that chelator. The inclusion of such a chelator in the culture medium thus not only extends the time taken to demonstrate that the product is pure, but also increases the expense of production by necessitating development of specific assays to prove that a "toxic" iron chelator does not contaminate the pure product.

It is apparent, therefore, that a need still exists to provide iron in a simple form to certain cells in culture at concentrations which will provide sufficient iron to enable continuing cell growth but which will not result in the precipitative damage discussed above. A further advantage would be to have a medium free of transferrin and lipophilic or nitrogen-containing chelators. The aim would be to achieve equivalent cell culture in a transferrin and lipophilic or nitrogen-containing chelator-free medium as would be obtained in a medium containing transferrin.

SUMMARY OF THE INVENTION

In order to satisfy the need to provide a transferrin free medium which supports the growth of certain cells, the present invention provides inter alia a method for culturing myeloma cells under agitated suspension culture in a medium containing iron but lacking transferrin or a lipophilic or synthetic nitrogen-containing chelator. The present invention shows that, surprisingly and contrary to the indications in the prior art, the iron requirements of a myeloma cell are different from those of a hybridoma cell, with the unexpected result that myeloma cells show continuous growth in concentrations of iron in the medium up to 100 times lower than that required for hybridoma cells. A further advantage of the method of the present invention is demonstrated by the improved titre of myeloma cell product obtained when cells are cultured in medium with low iron concentrations.

DESCRIPTION OF THE FIGURES

FIG. 2.

FIG. 3: FIG. 3a illustrates the growth of a hybridoma cell line in varying concentrations of ferric ammonium citrate under agitated suspension culture conditions and FIG. 3b shows the cell count and FIG. 3c shows a mathematically derived comparison of growth of the cell line so grown.

FIG. 4 illustrates the growth of a myeloma cell line in a rich serum-free, transferring-free medium in varying concentrations of ferric ammonium citrate under agitated suspension culture conditions.

In FIGS. 8A, 8B, 9 and 10, as in the other figures, the x axis defines the time in days and the y axis defines the viable cell number ($\times 10^5$ cells/mL).

DETAILED DESCRIPTION OF THE INVENTION

Figure 1A:
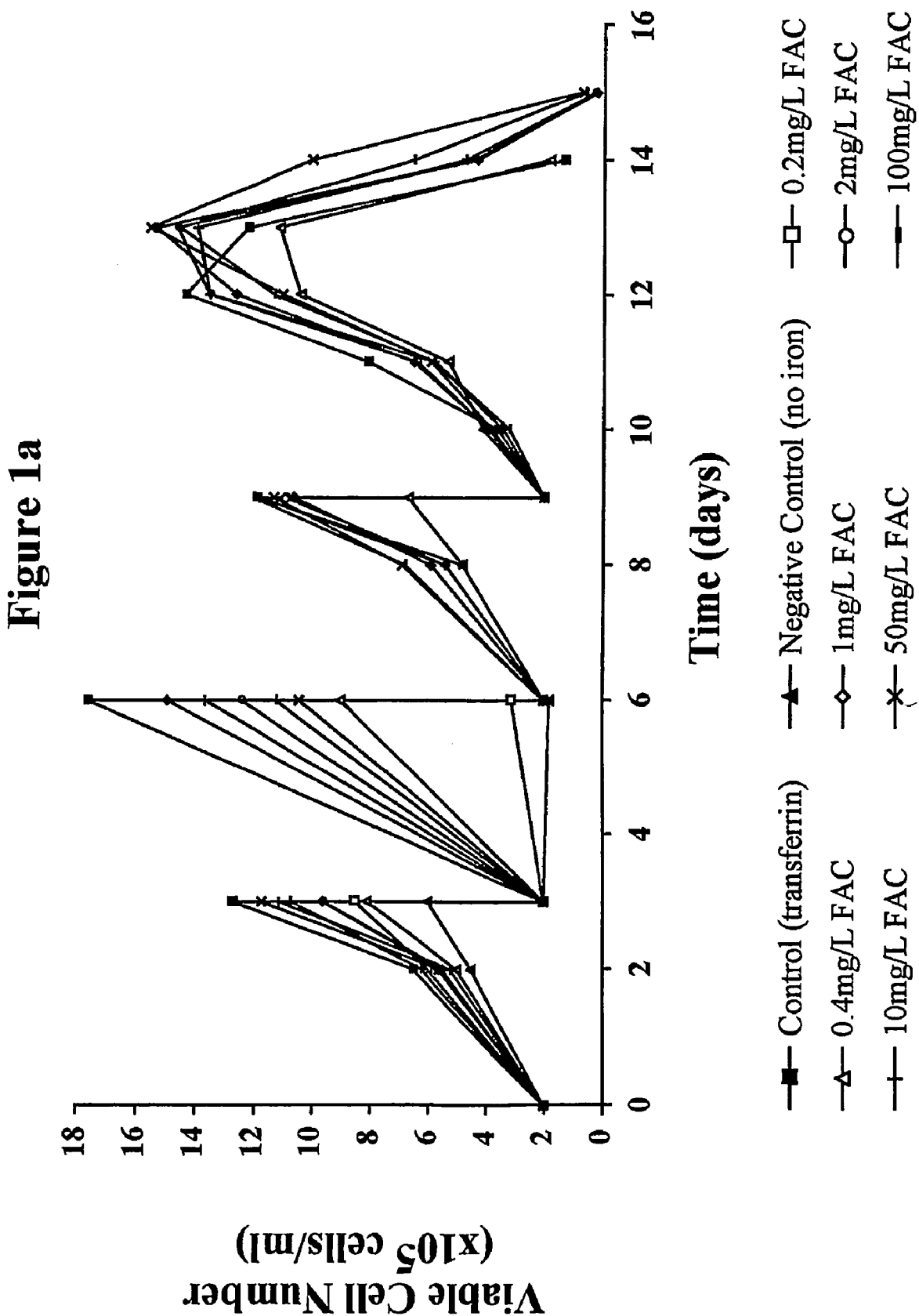
FIG. 1a illustrates the ability of a myeloma cell line to grow in varying concentrations of ferric ammonium citrate under agitated suspension culture conditions and FIG. 1b demonstrates the amount of antibody produced by a myeloma cell line grown in varying concentrations of ferric ammonium citrate.

In accordance with the above, the present invention provides in its first aspect, a method for the in vitro culture of a myeloma cell line which comprises:
(a) inoculating a culture medium with a myeloma cell line, said medium being capable of supporting the growth of said myeloma cell line and comprising iron at concentrations in the medium of from about 0.03 mg/L to about 3.2 mg/L, wherein said medium does not contain transferrin, a lipophilic chelator, a synthetic nitrogen-containing chelator or a lipophilic synthetic nitrogen-containing chelator; and
(b) growth of the inoculated culture medium under appropriate conditions and using agitated suspension culture.

In an embodiment of this aspect, the present invention provides a method for the in vitro culture of a myeloma cell line which comprises:
(a) inoculating a culture medium with a myeloma cell line, said medium being capable of supporting the growth of said myeloma cell line and comprising ferric ammonium citrate at a concentration in the medium of from about 0.2 mg/L to about 20 mg/L, wherein said medium does not contain transferrin, a lipophilic chelator, a synthetic nitrogen-containing chelator or a lipophilic synthetic nitrogen-containing chelator; and
(b) growth of the inoculated culture medium under appropriate conditions and using agitated suspension culture.

In a second aspect, the present invention provides a process for obtaining a mammalian cell product comprising culturing a myeloma cell capable of producing said product in a culture medium capable of supporting the growth of said myeloma cell line, said culture medium comprising iron at concentrations in the medium of from about 0.03 mg/L to about 3.2 mg/L, wherein said medium does not contain transferrin, a lipophilic chelator, a synthetic nitrogen-containing chelator or a lipophilic synthetic nitrogen containing chelator; and recovering said mammalian cell product.

In a yet further aspect, the present invention provides the use of a culture medium for supporting the in vitro growth of a myeloma cell line, wherein the culture medium comprises iron at concentrations in the medium of from about 0.03 mg/L to about 3.2 mg/L, wherein said medium does not contain transferrin, a lipophilic chelator, a synthetic nitrogen-containing chelator or a lipophilic synthetic nitrogen-containing chelator.

In an embodiment of these aspects of the invention, the medium contains ferric ammonium citrate at a concentration in the medium of from about 0.2 mg/L to about 20 mg/L.

In the present invention, the culture medium is capable of supporting the growth of a myeloma cell line. By "supporting growth", is meant the continuous growth of the cells over multiple subcultures with at least a doubling and preferably a tripling in cell number at each passage, i.e. from one subculture to the next. The number of subcultures is not essential to the present invention and depends on, for example, the length of the experiment being performed, or the product being produced. In the present invention, it is generally preferred that the cells show continuous growth over at least 2 subcultures, and preferably over at least 3 subcultures.

A myeloma cell, otherwise known as a lymphoid cell, is a cancerous lymphocyte which is typically immortal under normal growth conditions. Myeloma cell types are useful as they are excellent fusion partners for the production of monoclonal antibody producing hybridomas. In recent years, the importance of myeloma cell types as host cells in recombinant gene technology has become highly significant. This is particularly so with the use of the glutamine synthetase selectable marker, which is used with an NS0 myeloma host to produce stable high producing recombinant cell lines (Barnes et al. Cytotechnology 32: 109-123, 2000).

In the present invention, it is anticipated that any myeloma cell line can be used in the culture medium. It is generally preferred that the myeloma cell line is of mouse origin and, when so, it is particularly preferred that the myeloma is an NS0 cell line or a P3 series cell line, most preferably an NS0 cell line (such as ECACC 85110503). Other mouse myelomas include MOPC series, MPC-11, J558L, K6H6/B5, and 45.6.TG1.7. The method of the invention may also be used to culture rat and human myeloma cell types. Rat myeloma cell lines appropriate for use in the method of the invention include Y0 and Y, and appropriate human myeloma cell lines include HTK, RPMI 8226 and U266B1.

When the myeloma cell line is an NS0 cell, it is generally preferred that the cell line is transfected using the glutamine synthetase expression system.

The cell culture medium of the present invention does not contain either transferrin, a lipophilic chelator, a synthetic nitrogen-containing chelator or a lipophilic synthetic nitrogen-containing chelator. Lipophilic chelators may be defined for the purpose of this invention as chelators having two distinct properties: (1) they are hydrophobic, being poorly soluble or insoluble in water or a cell culture medium and often are aromatic and (2) they have a region of negative charge which allows 'binding' of iron through electrostatic interactions with positively charged iron ions. Examples of lipophilic chelators are tropolone and sodium nitroprusside. For the purpose of the present invention, synthetic nitrogen-containing chelators can be defined as iron binding compounds containing within their structure at least one nitrogen atom. Such compounds may be hydrophobic or hydrophilic. By "synthetic" in this respect is meant that the nitrogen-containing chelators are not naturally occurring, i.e. that they cannot normally be found in nature. Naturally occurring nitrogen-containing chelators which are made synthetically are not included within this definition and are not excluded from the methods and uses of the present invention. Such synthetic nitrogen-containing chelators include, but are not limited to, compounds such as ethylenediamine-tetraacetic acid (EDTA); ethyleneglycol-bis(p-aminoethyl ether)-N,N,N',N'-tetraacetic acid (EGTA); desferoxamine mesylate; diethylenetriaminepentaacetic acid (DTPA) and trans-1,2-diaminocyclohexane-N,N,N',N'-tetraacetic acid (CDTA). Also excluded from the methods and uses of the present invention are compounds which may be both lipophilic and synthetic nitrogen-containing chelators.

The exact composition of the medium is not important to the present invention, so long as the medium contains no transferrin, lipophilic chelator, synthetic nitrogen-containing chelator or lipophilic synthetic nitrogen-containing chelator, but does contain iron at the concentrations outlined above, and so long as the medium is capable of supporting the growth of a myeloma cell line, as previously defined.

Typically the cell culture medium will include sources of amino acids, vitamins, organic and inorganic salts and sugars. Compounds capable of providing these essential requirements for growth are commonly available and their incorporation into media for cell growth is within the skill of the person in the art based on information available in the art.

It is generally preferred that the cell culture medium be based on a known basal medium or derivative thereof which will support the continuous growth of mammalian cells. Such basal media are commonly available. Examples of appropriate basal media which may be supplemented to provide the medium of the present invention include Dulbecco's Modified Eagles Medium (DMEM), Hams F12 medium, Iscove's Modified Dulbecco's Medium and Roswell Park Memorial Institute (RPMI).

The medium of the present invention may be serum free, protein free, free of components of animal derivation or chemically defined.

In an alternative, the cell culture medium may be produced from first principles by combination of the specific components required for continuous growth.

When preparing a cell culture medium for a specific cell type or cell line, a basal medium will typically be modified or supplemented depending on the requirements of the particular cell type/line. The choice of supplements is within the skill of the person in the art and does not form an essential aspect of the present invention. Typically such supplements may include lipids (e.g. cholesterol and fatty acids), lipid precursors (e.g. ethanolamine) growth promoters or regulators (e.g. insulin), trace elements (e.g. selenium), polymers (e.g. pluronic F-68) and glutamine in the case of glutamine dependent cell types.

One example of a medium to which an iron source can be added in order to provide iron to the medium at the concentrations outlined above to render it suitable for use in the present invention is a cell culture medium based on CDSS described by Qi et al. in Cytotechnology 21:95-109 (1996). This medium, known as modified CDSS, is based on DMEM/F12 (1:1) (Gibco BRL. 1× liquid cat. no. 21331) with the following additions: GS supplement (JRH cat. no. 58672) 40 ml/L; Clevelands trace elements I (Cellgro 99-175) 0.5 ml/L; Clevelands trace elements II (Cellgro 99-176) 1 ml/L; Zinc Sulphate 2 µM; Sodium Selenite 50 nM; Ethanolamine 2 µM; Pluronic F68 1 g/L; Sodium bicarbonate 1.3 g/L and 2M hydrochloric acid 3.6 ml/L. The medium also contains 6 mM glutamine for cell lines not capable of glutamine independent growth and 2 ml/L cholesterol lipid concentrate (Gibco cat. no. 00-0061) for NS0 cell lines.

The cell culture medium of the present Invention comprises iron at a concentration in the medium of from about 0.03 mg/L to about 3.2 mg/L. In a preferred embodiment, the iron source in the culture medium is a soluble iron compound. The amount of soluble iron compound used should be that sufficient to provide iron at that concentration to the medium and, so long as the amount of iron in the medium is within that range, should be just sufficient to support growth of the cells. The exact concentration of soluble iron compound in the medium may vary depending on the specific soluble iron compound being used and the cell line in use and/or other medium components present. The appropriate concentration can be determined in a straightforward manner, for example by performance of small-scale experiments in accordance with conventional practice, such as a dose response to the soluble iron compound in a particular medium with a particular cell line.

In the present invention, the concentration of the iron in the medium, preferably provided by a soluble iron compound, is from about 0.03 mg/L to about 3.2 mg/L, preferably from about 0.03 mg/L to about 2.4 mg/L, more preferably from about 0.064 mg/L to about 1.6 mg/L and most preferably from about 0.16 mg/L to about 0.32 mg/L.

In a preferred embodiment of the present invention, the source of iron in the medium is a soluble iron compound. Appropriate soluble iron compounds are soluble in water or the cell culture medium but exhibit limited solubility in organic solvents. Such compounds are commonly available to the person skilled in the art, for whom a determination of solubility is straightforward.

The present invention also envisages the use of any alternative iron source, so long as the iron source is capable of providing sufficient iron to the cells to enable continuous growth in the absence of transferrin or a lipophilic or synthetic nitrogen-containing chelator.

Appropriate soluble iron compounds for provision of iron and hence for use in the present invention include ferric and ferrous salts or simple chelates thereof. It is to be noted that "simple chelates" as used herein does not include the lipophilic or synthetic nitrogen-containing chelators discussed hereinabove. The term "simple chelates" is used herein in a comparable fashion to the use of the term "simple iron carriers" in various pieces of the prior art.

Examples of ferric or ferrous salts or simple chelates thereof, which can be the iron source in the culture medium for the methods and uses of the invention, include ferrous sulphate, ferrous citrate, ferric citrate, and ferric ammonium compounds. Preferred for use in the present invention are ferric ammonium compounds. Specific ferric ammonium compounds appropriate for use in the present invention include ferric ammonium citrate, ferric ammonium oxalate, ferric ammonium fumarate, ferric ammonium malate and ferric ammonium succinate. Most preferred for use in the present invention is ferric ammonium citrate.

Although the medium of the present invention may contain more than one source or iron, for example a mixture of appropriate iron containing compounds, it is generally preferred that, when that iron source is a soluble iron compound, there is only one such compound in the medium.

In a preferred embodiment of the present invention, the soluble iron compound is ferric ammonium citrate. Typically, in this embodiment and in order to provide iron to the medium in the range from about 0.03 mg/L to about 3.2 mg/L, the ferric ammonium citrate will be used at concentrations of from about 0.2 mg/L to about 20 mg/L, preferably from about 0.2 mg/L to about 15 mg/L, more preferably from about 0.4 mg/L to about 10 mg/L and most preferably from about 1 mg/L to about 2 mg/L.

In a preferred embodiment of the present invention, the culture medium contains a ferric ammonium compound. The results of the present invention have demonstrated that such ferric ammonium compounds, in particular ferric ammonium citrate, are used more efficiently by the cells than, for example, ferric citrate. In particular, if ferric citrate is used, this must be present at 10 times the concentration of a ferric ammonium compound in an equivalent culture medium. This is demonstrated by FIGS. 1 and 2 of the present invention, from which it is apparent that for continuous cell growth over at least 3 passages, ferric citrate must be present at concentrations of at least 10 mg/L, whereas ferric ammonium citrate provides the same level of growth at concentrations of 0.2 mg/L. It is also noteworthy that antibody titre is best at lower iron concentrations.

The cell culture medium of the present invention may be prepared by appropriate mixture of the individual components using standard practice. The media may also be prepared in different forms such as a liquid form or as a dry powdered medium for reconstitution before use. Culture media of the present invention are stable when stored under appropriate conditions.

Accordingly, the present invention also provides a method for the preparation of a cell culture medium capable of supporting the in vitro growth of a myeloma cell line, said medium comprising iron at concentrations in the medium of from about 0.03 mg/L to about 3.2 mg/L, wherein said medium contains no transferrin, lipophilic chelator, synthetic nitrogen-containing chelator or lipophilic synthetic nitrogen-containing chelator; which comprises admixture of the individual components thereof.

The cell culture medium of the present invention is appropriate for use in a variety of culture conditions. Thus, the medium can sustain the growth of a myeloma cell line in monolayer and suspension, particularly agitated suspension, culture. Agitated suspension culture may be defined as cell culture in which a homogeneous suspension of cells in the culture medium is assisted by means of an agitating force. Means of applying an agitated force are well known in the art and include, for example, a mechanically stirred impeller and/or sparging of gas for bioreactor cultures, and maintenance of cell culture flasks on a reciprocal shaking platform. The medium according to the invention is particularly suited to the culture of cells in agitated suspension culture, i.e. in suspension using a suitable agitated culture vessel, for example a stirred tank or airlift fermenter, using known culture techniques.

Accordingly, the present invention also provides a culture medium capable of supporting the growth in agitated suspension culture of a myeloma cell line, the medium comprising iron at concentrations in the medium of from about 0.03 mg/L to about 3.2 mg/L, wherein the medium contains no transferrin, lipophilic chelator, synthetic nitrogen-containing chelator or lipophilic synthetic nitrogen-containing chelator.

The prior art has taught that myeloma and hybridoma cell types have the same requirements when it comes to iron in a culture medium. Our results indicate that this is not so. FIG. 3 illustrates the growth of a hybridoma cell line in a culture medium containing ferric ammonium citrate. As may be seen from this figure, the growth of the hybridoma cells corresponds with the expectations of the art, i.e. there is good growth of the cells at high concentrations of ferric ammonium citrate (50 mg/L and 100 mg/L), but not at lower concentrations of this soluble iron compound (less than 10 mg/L). When this is compared with FIG. 1, illustrating the growth of myeloma cells in media with equivalent concentrations of a soluble iron compound, it becomes apparent that hybridoma cells require approximately 100 times more iron in the medium than do myeloma cells for comparable growth.

A further advantage of the methods of the present invention is the improved titre of a myeloma cell product when the myeloma cell is cultured in a low iron-containing medium, i.e. when the cell line is cultured according to the method of the invention. The examples following demonstrate that the titre of the myeloma cell product is unexpectedly higher when the concentration of iron in the medium is low, for example between 0.03 mg/L and 3.2 mg/L, preferably between 0.16 mg/L and 0.32 mg/L.

Cell products which may be obtained according to the invention include any products which are produced by cultured mammalian cells. Typical products include, for example, polypeptides and proteins, for example immunoglobulins such as monoclonal and recombinant antibodies and fragments thereof, hormones such as erythropoietin and growth hormone, e.g. human growth hormone, lymphokines such as interferon, interleukins such as interleukin 2, 4, 5 and 6 and industrially and therapeutically useful enzymes such as tissue plasminogen activator. Methods for the manipulation of myeloma cells by genetic recombinant techniques so that they are capable of producing said cell products are widely used and commonly available in the art.

In order to obtain cell products, myeloma cells capable of producing such products are grown in the medium of the invention. The conditions for growth will depend on, for example, the cell line being used and the product to be produced, but will be readily determinable using knowledge available in the art.

To this end, the present invention also provides the use of a culture medium comprising iron at concentrations in the medium of from about 0.03 mg/L to about 3.2 mg/L, wherein said medium does not contain transferrin, a lipophilic chelator, a synthetic nitrogen-containing chelator or a lipophilic synthetic nitrogen-containing chelator for the preparation of a mammalian cell product.

Methods for the isolation of the cell product being produced from the myeloma cells and/or culture medium are well known and in common practice in the art.

All references mentioned herein are expressly incorporated by reference in their entirety. It is to be understood that while the invention has been described in conjunction with the above embodiments, that the foregoing description and the following examples are intended to illustrate and not limit the scope of the invention. Other aspects, advantages and modifications within the scope of the invention will be apparent to those skilled in the art to which the invention pertains.

EXAMPLES

Example 1

Ferric Ammonium Citrate (FAC) at 0.2 mg/L is Able to Support Continuous Growth of GS-NS0 Cell Lines Methods A recombinant GS-NS0 mouse myeloma cell line (Cell line A) expressing a human IgG antibody using the glutamine synthetase (GS) expression system (European Patent Specification No. 2560550) previously subcultured in a proprietary serum free medium (GSF medium) containing a chelated source of iron was centrifuged and resuspended in chelator-free medium. Cells resuspended in this medium were then used to inoculate experimental flasks at an inoculation density of $2\times10^5$ cells/ml.

The experiment was carried out using 250 ml Erlenmeyer flasks (working volume between 20 and 50 ml) with vented caps incubated in a reciprocal shaker at 36.5° C. and 125 rpm with an atmosphere of 5% $CO_2$/95% air and 75% humidity.

Individual flasks containing modified CDSS medium were supplemented using stock solutions of FAC to give flasks containing FAC at final concentrations of 0.2, 0.4, 1, 2, 10, 50 and 100 mg/L. The stock solutions of FAC were prepared in water at concentrations of 0.5 (for flasks containing 0.2 to 2 mg/L FAC) and 25 mg/L (for flasks containing 10 to 100 mg/L FAC). Stock solutions were filter sterilised before addition to flasks.

A flask containing modified CDSS medium supplemented with 1 mg/L human transferrin and 0.1 mg/L FAC was included as a positive control. A flask containing modified CDSS medium without any transferrin or FAC supplements was included as a negative control. All flasks were supplemented with 2 ml/L cholesterol lipid concentrate (Gibco) as a source of cholesterol. Cholesterol lipid concentrate is an emulsion of cholesterol and fatty acids complexed with cyclodextrin.

Flasks were subcultured three times in order to minimise any effects of carry over of chelated/stored iron from the inoculum. Flasks were subcultured by dilution with fresh medium back to $2\times10^5$ cells/ml at 3 day intervals. On the third subculture flasks were allowed to follow the full growth cycle until low viability was reached (this is often referred to as an overgrow). Cell counts were performed using an Innovatis Cedex cell counter. Antibody titre was determined using a sandwich ELISA against a homologous IgG standard.

Results

FIG. 1a shows the cell concentration during the subculturing and final overgrow for the range of FAC concentrations tested. This figure clearly shows that the negative control culture was unable to proliferate beyond the first subculture. The culture containing 0.2 mg/L FAC was able to proliferate after the first division, but was then unable to grow further. The fact that these cultures were able to grow after the initial inoculation is probably a result of cell storage of iron that requires depleting by cell division.

FIG. 1a also clearly shows that concentration equal to and in excess of 0.4 mg/L was able to support continuous cell growth over several subcultures and during the overgrow culture. FIG. 1c shows that in a duplicate of this experiment, a FAC concentration of 0.2 mg/L was able to support continuous cell growth.

Figure 1B:
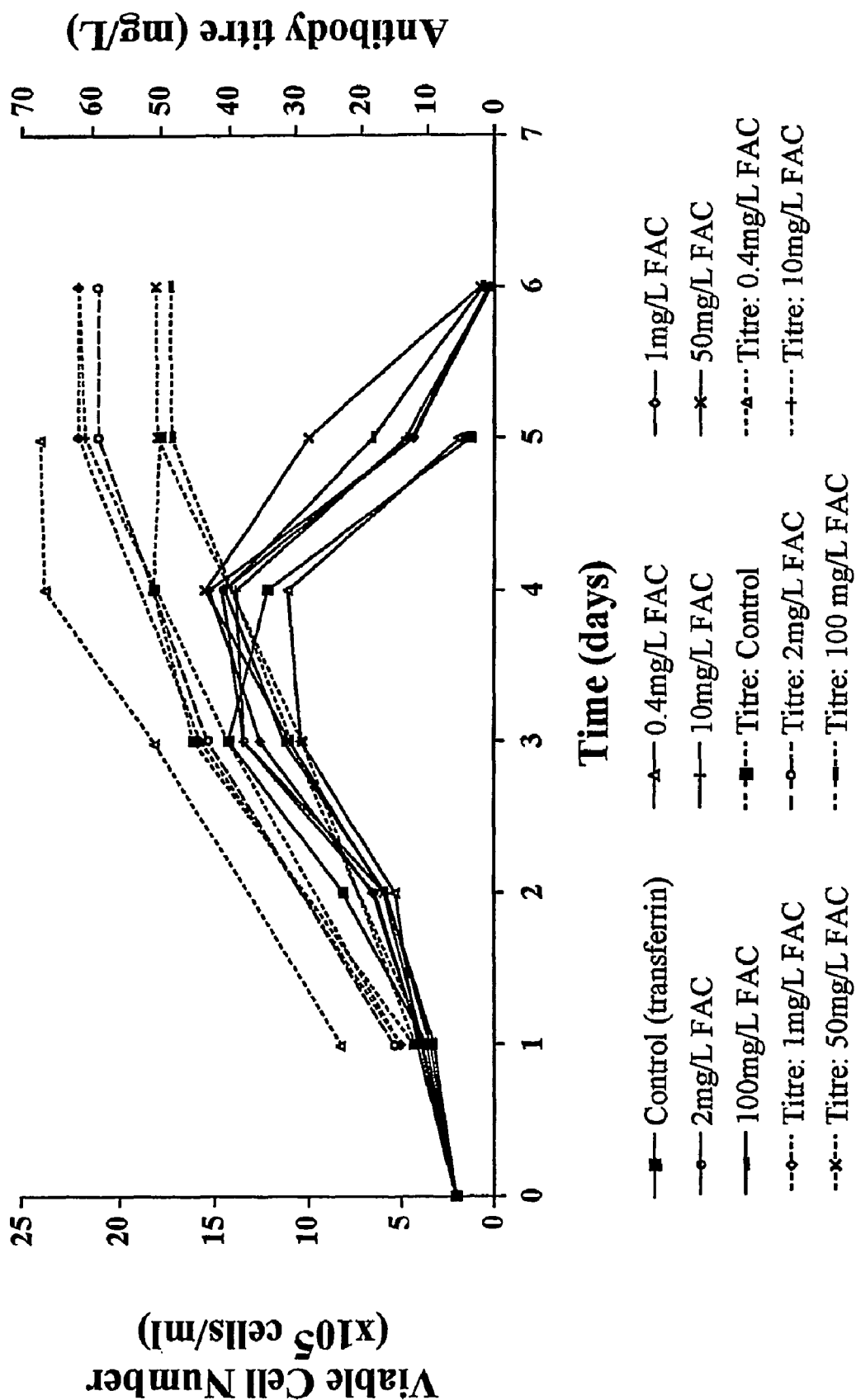
FIG. 1.
FIG. 1c shows growth data from a duplicate of this experiment.
Figure 1C:
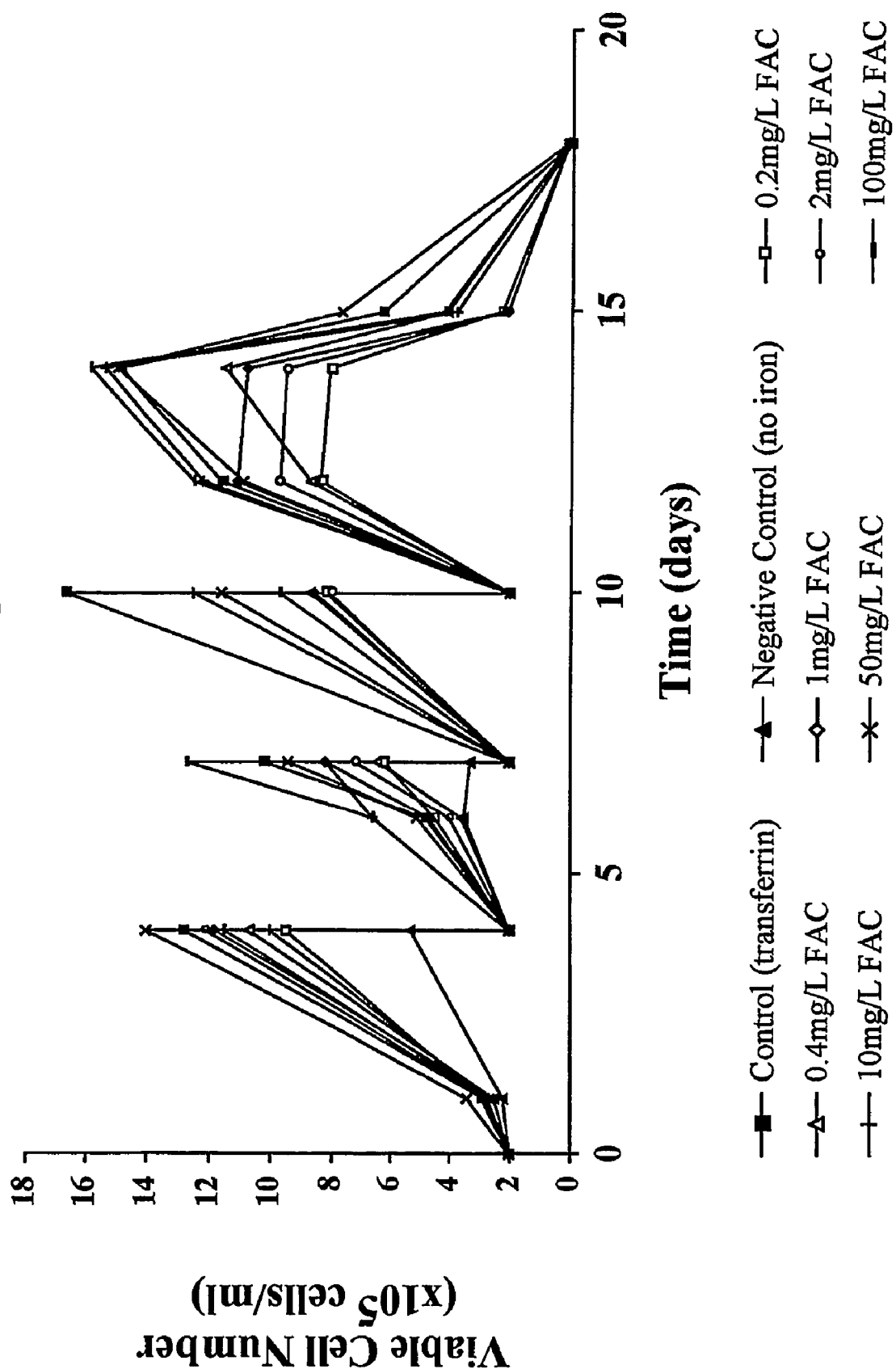

FIG. 1b shows the cell count and antibody production data for the overgrow cultures from the first of the duplicates. This figure shows that growth equivalent to transferrin containing control, in terms of maximum viable cell number and the area underneath the growth curve, was achieved with FAC concentrations of 1 mg/L and greater. This indicates that after a threshold level (1 mg/L) is reached, growth is largely equivalent over a large range of FAC concentrations. However, at a FAC concentration of 10 mg/L, a small amount of rust coloured precipitate was observed. At 50 and 100 mg/L this precipitate was observed in much larger quantities. This precipitate is presumably iron hydroxide as warned against by Bertheussen (Cytotechnology 11: 219-231, 1993).

FIG. 1b also shows the antibody titre as determined by sandwich ELISA. This shows that when compared to the transferrin containing control, the cultures containing FAC produced at least as much, and in the majority of the cases significantly more antibody. The antibody titre obtained in the FAC containing cultures also showed an inversely proportional relationship with FAC concentration, for example the culture containing 0.4 mg/L FAC produced over 30% more antibody than the culture containing 100 mg/L FAC.

Example 2

Ferric Citrate (FC) is Required at a Concentration One Order of Magnitude Higher than FAC in Order to Support Continuous Growth of GS-NS0 Cell Lines Methods The methodology of example 2 was identical to that of example 1, the only exception being the source of chelated iron. In this example, ferric citrate (FC) was used in place of FAC.

FC is only slowly soluble in cold water. To prepare stock solutions of FC it was therefore necessary to dissolve FC in water maintained at 80° C., with agitation, for up to 2 hours. Stock solutions were prepared at concentrations of 0.5 (for flasks containing 0.2 to 2 mg/L FAC) and 10 mg/L (for flasks containing 10 to 100 mg/L FAC).

Results

Figure 2A:
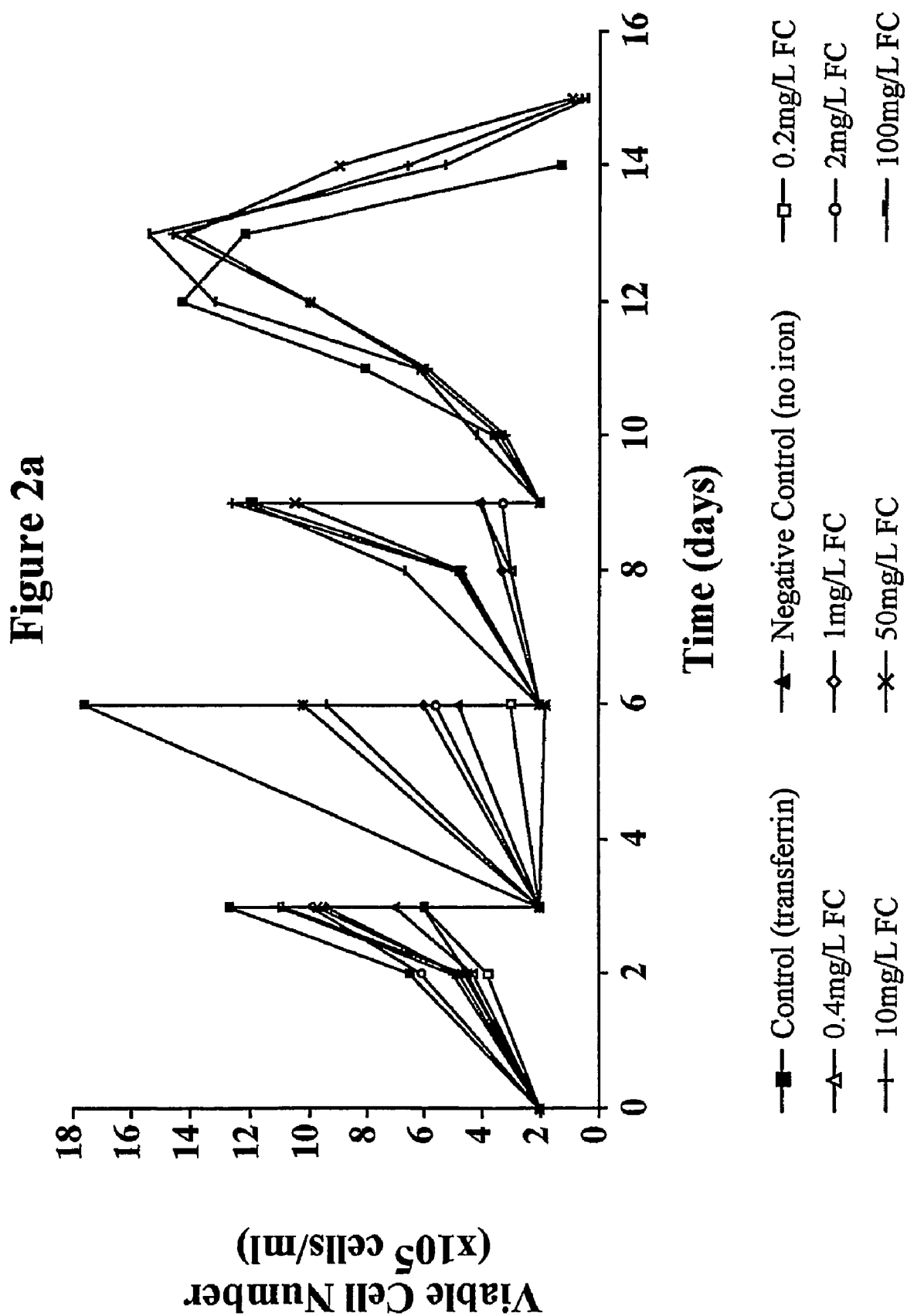
FIG. 2a illustrates the growth of a myeloma cell line in varying concentrations of ferric citrate under agitated suspension culture conditions and FIG. 2b shows the cell count and antibody titre of the cell line so grown.

FIG. 2a shows the cell concentration during the subculturing and final overgrow for the range of FC concentrations tested. This shows that the negative control culture and the culture containing 0.2 mg/L FC were unable to proliferate beyond the first subculture. The cultures containing 0.4, 1 and 2 mg/L FC were unable to proliferate beyond the second subculture. Thus, for the concentrations tested, FC is required at a concentration of 10 mg/L or greater to support continuous cell growth over several subcultures and during the overgrow culture.

Figure 2B:
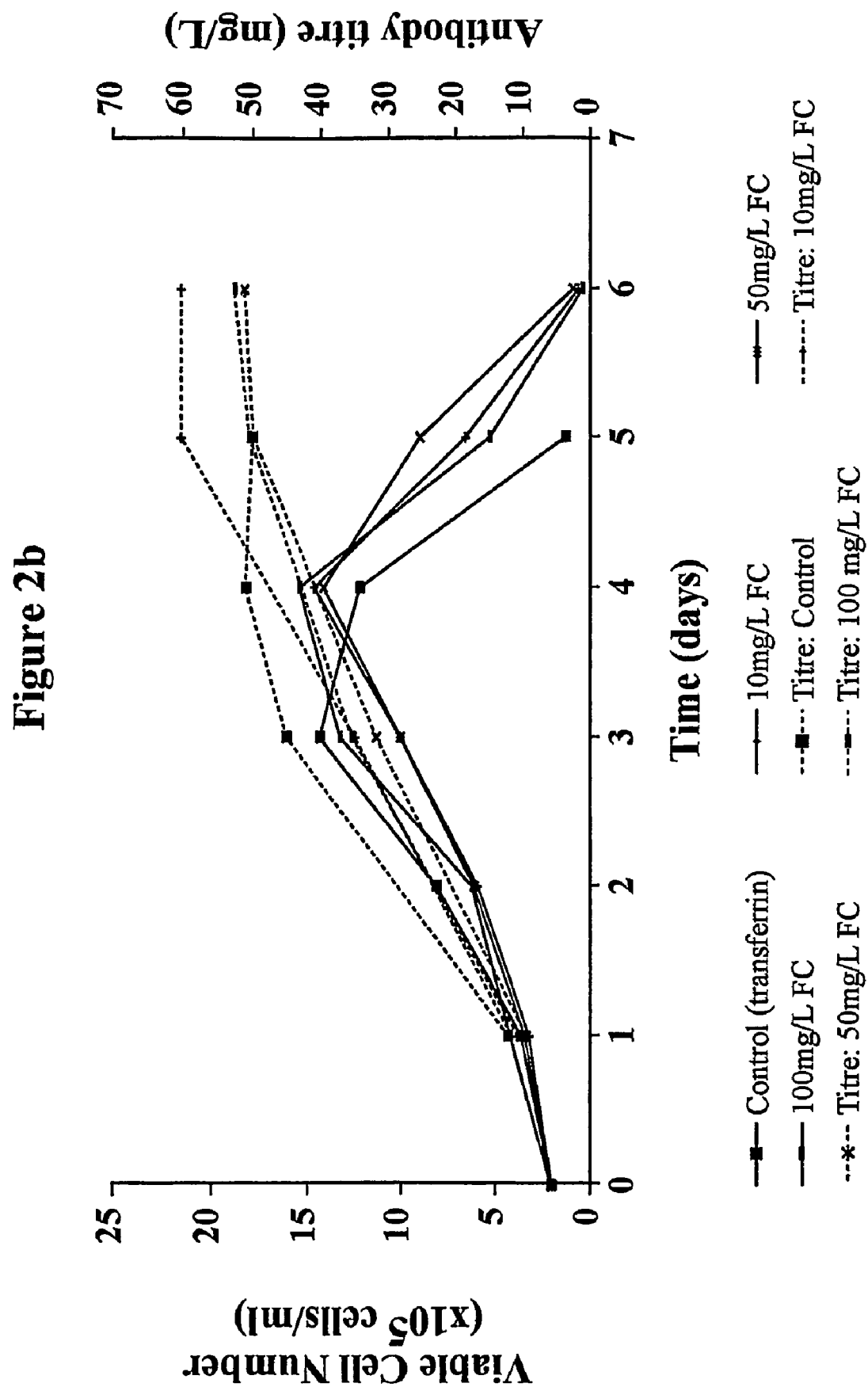

FIG. 2b shows the cell count and antibody production data for the overgrow cultures. This figure shows that growth equivalent to transferrin containing control, in terms of maximum viable cell number and the area underneath the growth curve, was achieved with FC concentrations of 10 mg/L and greater. As with FAC, a rust coloured precipitate was observed in cultures containing 10 mg/L FC and greater.

FIG. 2b also shows the antibody titre as determined by sandwich ELISA. This shows that when compared to the transferrin containing control, the cultures containing FC produced at least as much, and in the case of 10 mg/L FC significantly more antibody. As observed with FAC the lowest concentration of FC gave the highest titre.

This result shows that in order to support cell growth equivalent to that observed with transferrin, FC is required at a concentration 10× higher than FAC.

Example 3

Hybridoma Cell Lines Require FAC at a Concentration in Excess of Two Orders of Magnitude Higher than GS-NS0 Cell Lines to Obtain Continuous Cell Growth in Agitated Suspension Culture Methods The methodology of example 3 was identical to that of example 1, with the following exceptions:

A mouse hybridoma cell line (9E10), producing anti-Myc antibody, previously subcultured in modified CDSS supplemented with 1 mg/L human transferrin and 6 mM Glutamine was used to inoculate experimental flasks at an inoculation density of $1\times10^5$ cells/ml.

The experiment was carried out using 250 ml Erlenmeyer flasks with sealed caps incubated in a reciprocal shaker at 36.5° C. and 125 rpm. Flasks were gassed initially and at 2 day intervals with 5% $CO_2$/95% Air.

Flasks were not supplemented with cholesterol lipid concentrate since this hybridoma cell line does do not require cholesterol, Flasks were subcultured by dilution with fresh medium back to $1\times10^5$ cells/ml at 3 day intervals. On the third subculture flasks were allowed to overgrow. Cell counts were performed using the trypan blue exclusion method.

Results

FIG. 3a shows the cell concentration during the subculturing and final overgrow for the range of FAC concentrations tested. This shows that the negative control culture and the cultures containing 0.2 and 0.4 mg/L FAC were unable to proliferate beyond the first subculture. The cultures containing 1, 2 and 10 mg/L FAC were unable to proliferate beyond the second subculture. Thus, for the concentrations tested, FAC is required at a concentration of 50 mg/L or greater to support growth.

Figure 3B:
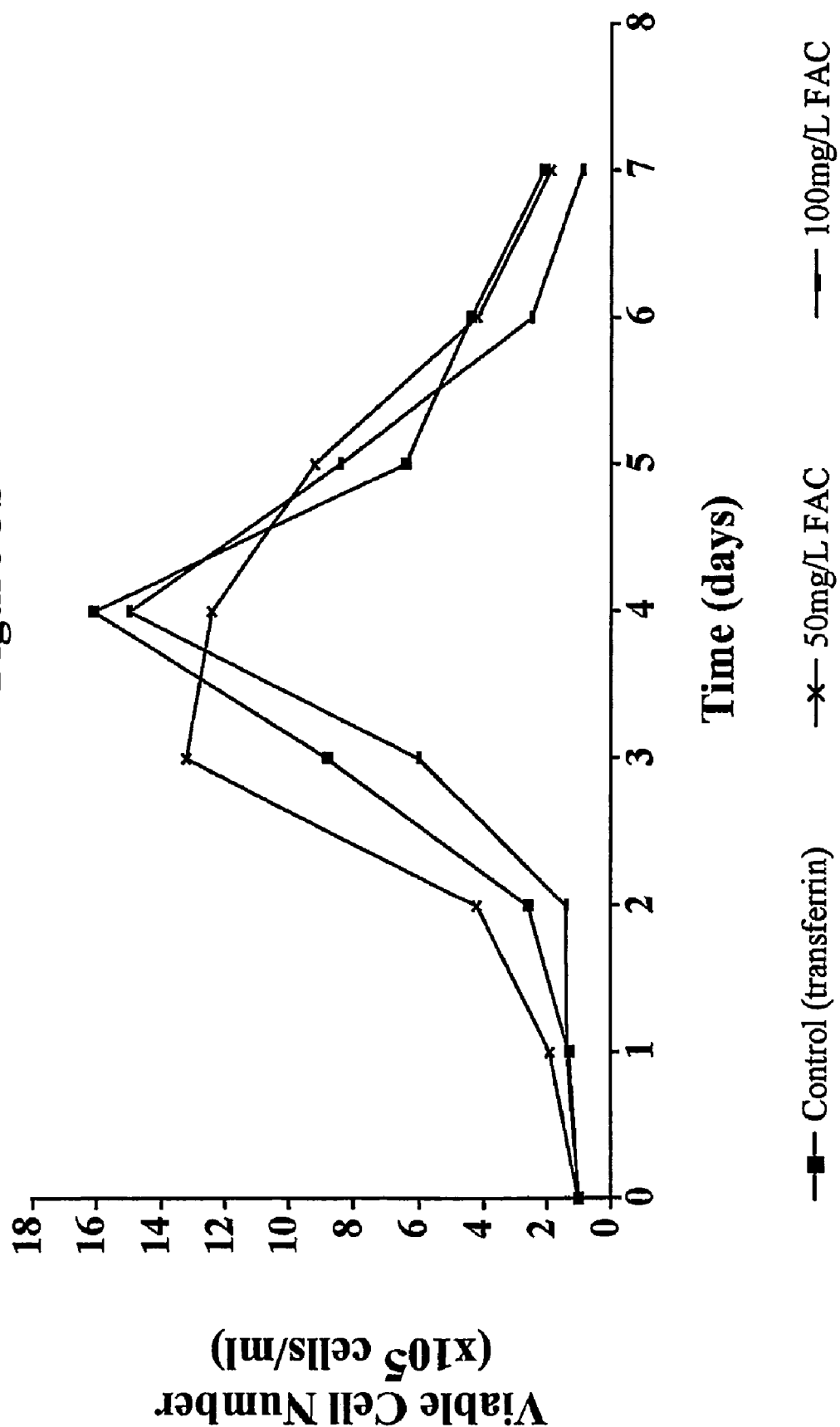
Figure 3C:
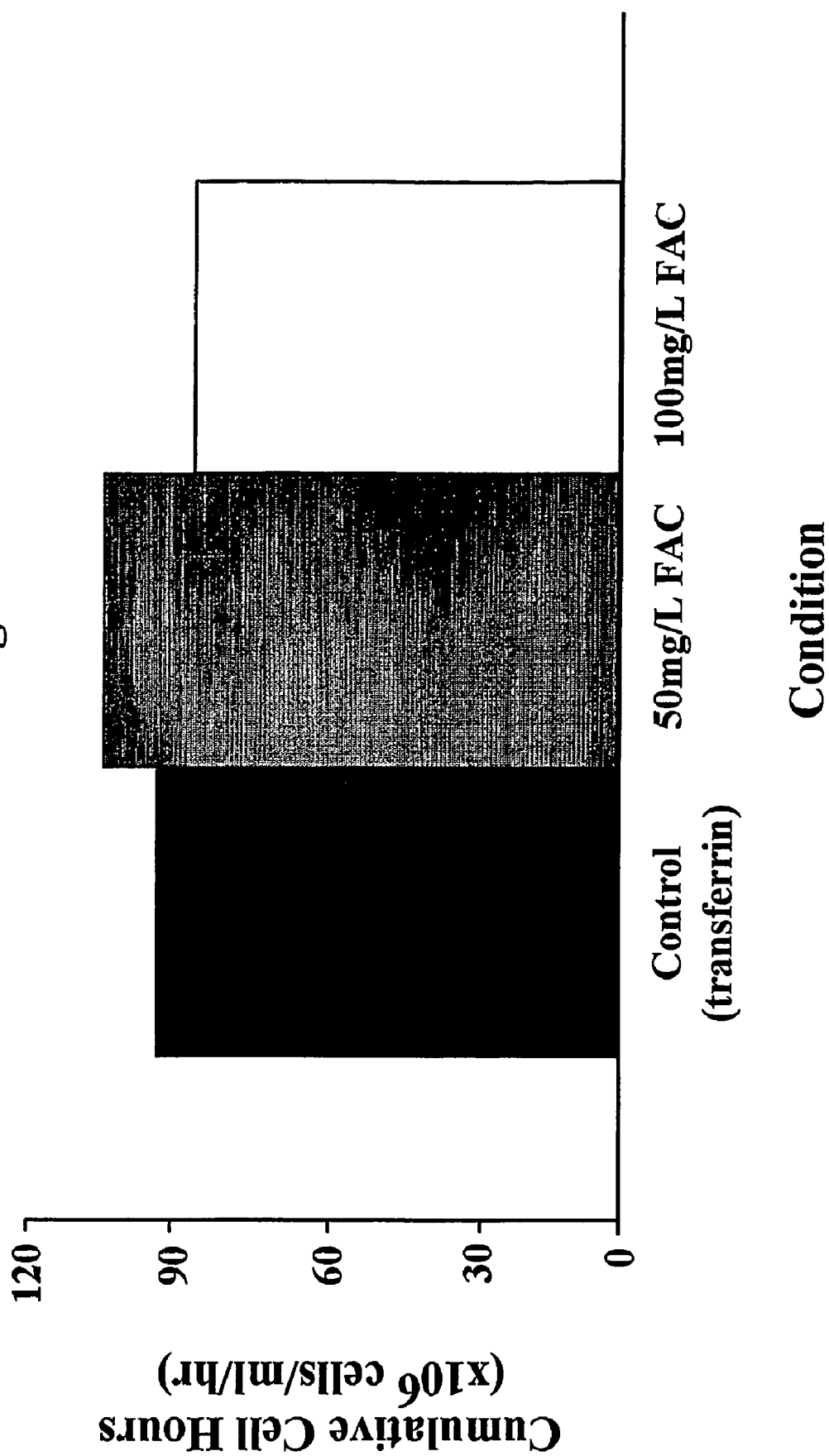

FIG. 3b shows the cell count of overgrow cultures. This figure shows that to obtain growth equivalent to transferrin containing control, in terms of maximum viable cell number, 100 mg/L FAC was required. However, if growth is considered in terms of the integral of the area underneath the growth curve (calculated by summation of the areas approximated to a right angle trapezium), or cumulative cell hours (CCH), equivalent growth to transferrin containing control is observed at 50 mg/L FAC. This is shown clearly in the bar chart showing maximum CCH (FIG. 3c). As observed previously, a rust coloured precipitate was seen in cultures containing 50 and 100 mg/L FAC.

This result shows that for continuous cell growth in agitated suspension culture, hybridoma cell lines require FAC at a concentration in excess of 100× higher than GS-NS0 cells.

Example 4

FAC is an Effective Source of Iron when Used in Rich Medium Capable of Supporting Cell Growth and Antibody Titres to High Levels Example 4 further shows the utility of FAC as a source of iron. In this example FAC is used as the sole source of iron in a proprietary serum free medium (containing bovine serum albumin [BSA] as the only non-defined component), known as GSF, using a second, antibody producing, recombinant GS-NS0 cell line (Cell line B).

Methods

Cells previously cultured in a proprietary serum free medium containing 10 μM tropolone (a lipophilic iron chelator [see WO94/02592]) and 0.4 mg/L FAC as the iron source, were centrifuged and resuspended in tropolone and iron free GSF serum free medium. Cells resuspended in this medium were then used to inoculate experimental flasks at an inoculation density of $2\times10^5$ cells/ml.

The experiment was carried out using 250 ml Erlenmeyer flasks (working volume 50 ml) with sealed caps incubated in a reciprocal shaker at 36.5° C. and 125 rpm. Flasks were gassed initially and at 2 day intervals with 5% $CO_2$/95% Air.

Individual flasks containing GSF (tropolone and iron free) medium were supplemented using a 1 mg/ml stock solution of FAC to give flasks containing FAC at final concentrations of 0.2, 0.4, 0.8 1.2, 1.6 and 2 mg/L. The stock solution was filter sterilised before addition to flasks. A flask containing medium supplemented with 5 μM tropolone and 0.4 mg/L FAC (previously shown to be equivalent to transferrin) was included as a positive control.

All flasks were also supplemented with 1 ml/L of a 1000× concentrated cholesterol and fatty acid supplement (CLOC).

Flasks were subcultured by dilution with fresh medium back to $2\times10^5$ cells/ml at 5 day intervals. On the second subculture flasks were allowed to overgrow to saturation. Cell counts were performed using the trypan blue exclusion method. Antibody titre analysis was performed using analytical protein A hplc against a homologous standard.

Results

Figure 4:
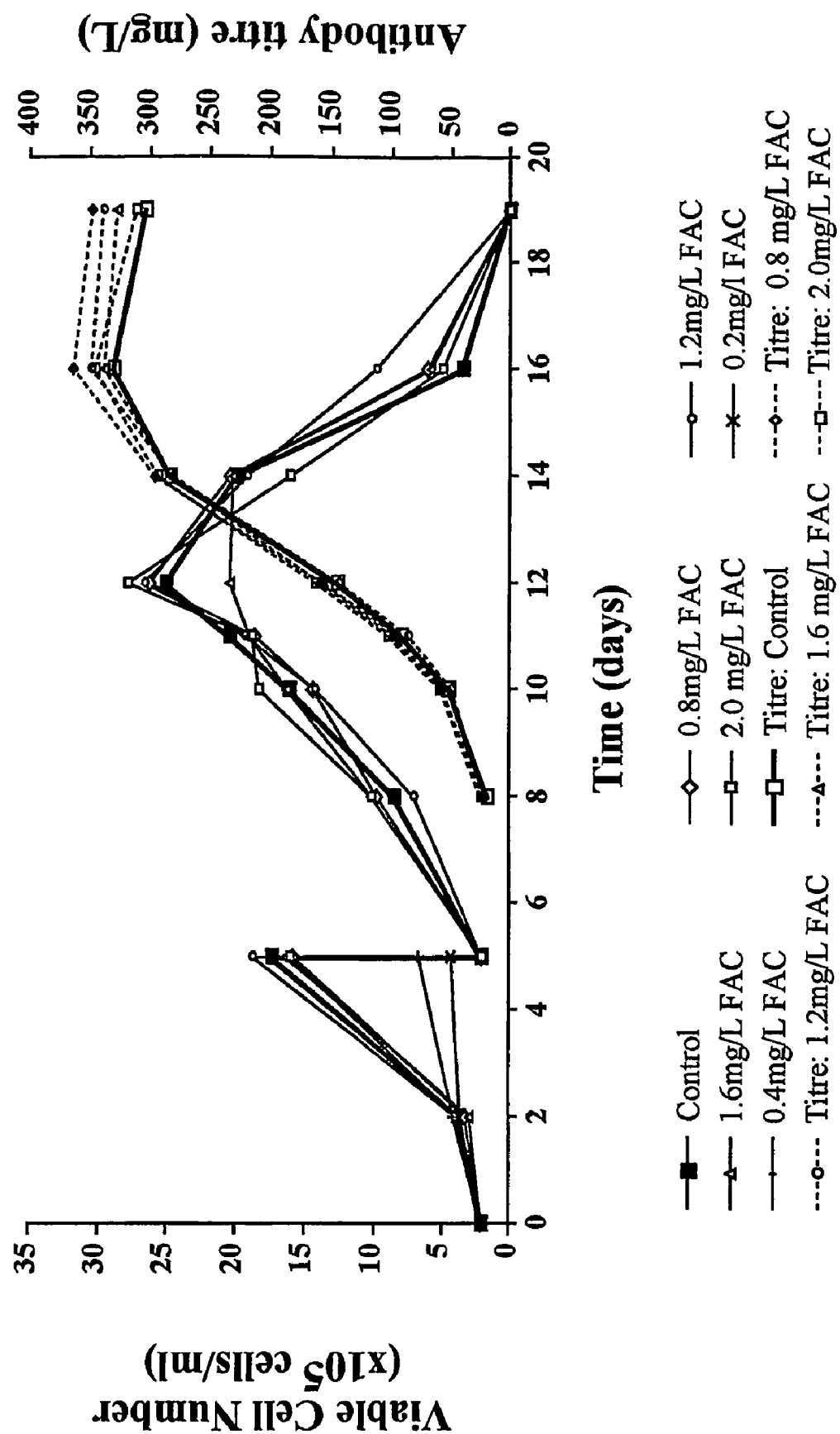
FIG. 4.

FIG. 4 shows the cell concentration during the subculturing and final overgrow for the range of FAC concentrations tested. This figure shows that medium containing FAC at concentrations of 0.8 mg/L and above could support growth equivalent to that observed in the positive control culture. FIG. 4 also shows antibody production in the overgrow cultures. This shows that FAC at 0.8 mg/L and greater was capable of supporting antibody production at least equivalent to control. The trends in antibody production were also very similar to those seen in Examples 1 and 2.

This result shows that FAC is effective when used in rich medium capable of supporting cell growth and antibody titres to high levels.

Example 5

Medium Containing FAC as an Iron Source is Able to Support Growth and Antibody Production in a Scaled Down Version of a Production System Methods Fermentations of cell line B were carried out using GSF serum free medium containing 5 μM tropolone and 0.4 mg/L FAC (control), or 1.0 mg/L FAC. Fermentations were carried out in 7 L (4.5 L working volume) Applikon fermenters fitted with a hemispherical bottom and stirred at 150 rpm using a marine impeller. Fermentations were operated at 36.5° C., pH 7.1 and sparged with air/oxygen to maintain a dissolved oxygen tension of 15%.

Innoculum for these fermentations was provided by subculture of the cells in media homologous to that used in the fermentations.

Results

Figure 5:
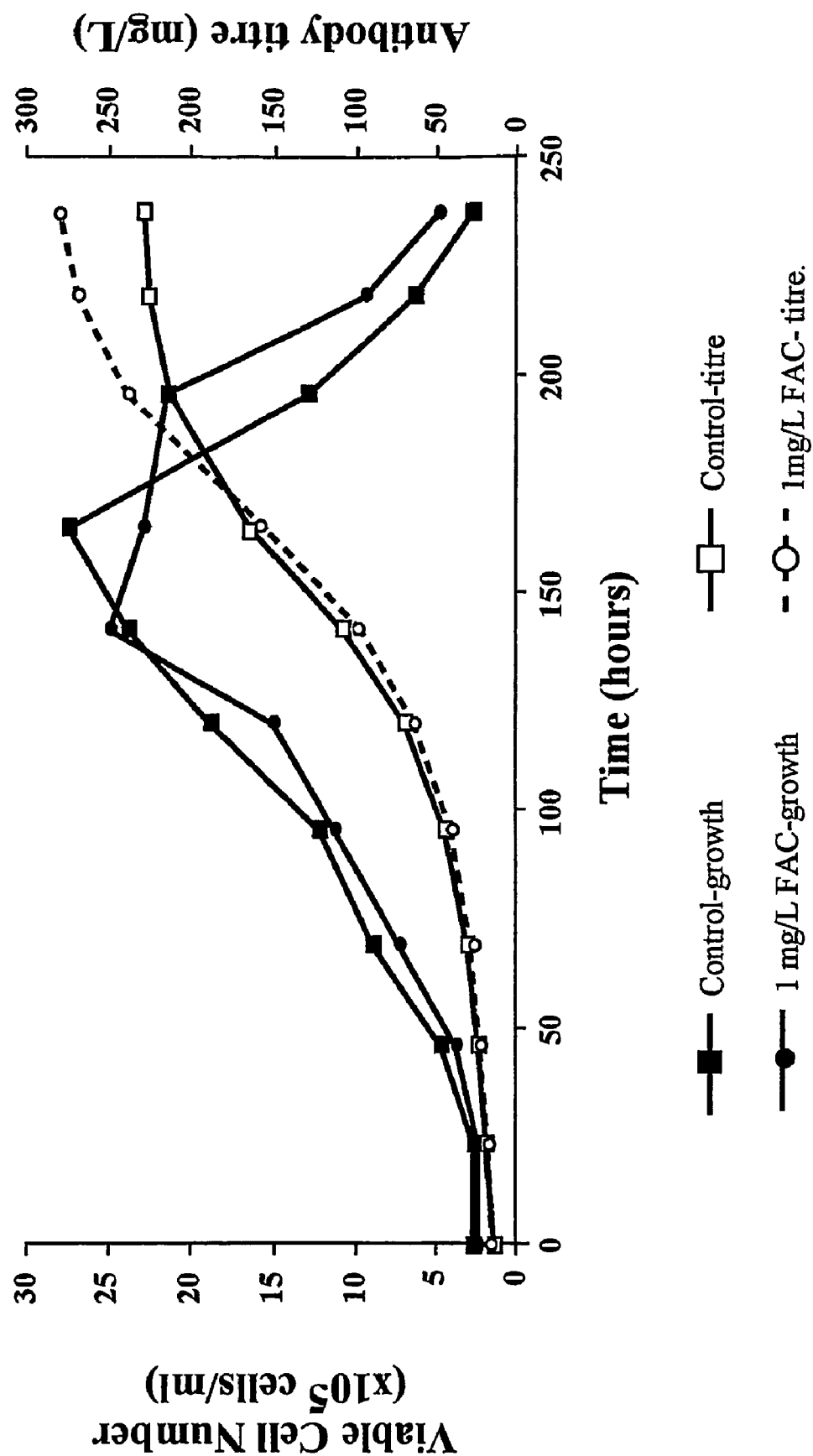
FIG. 5: illustrates the ability of ferric ammonium citrate to provide all required iron for growth of a myeloma cell line under agitated suspension fermentation growth conditions.

FIG. 5 shows that similar cell growth and production characteristics were observed when using medium supplemented with either 5 μM tropolone/0.4 mg/L FAC (control) or 1 mg/L FAC in stirred, sparged fermentation vessels.

This result demonstrates the utility of FAC as an iron source in a scale down version of the production system.

Example 6

FAC can Support Growth to High Cell Densities and Production to High Titres in Protein Free Medium Methods A comparison of GSF serum free (protein [BSA] containing) and protein free GSF medium each containing 1 mg/L FAC was carried out using stirred, sparged, fed batch fermentations of cell line A (see example 1). Protein free fermentations were supplemented with 2 m/L cholesterol lipid concentrate (see example 1), and serum free fermentations were supplemented with 1 ml/L of the CLOC supplement (see example 4). Fermentation conditions were as described in Example 5. Innoculum for these fermentations was provided by subculture of the cells in media the same as that used in the fermentations.

Results

Figure 6:
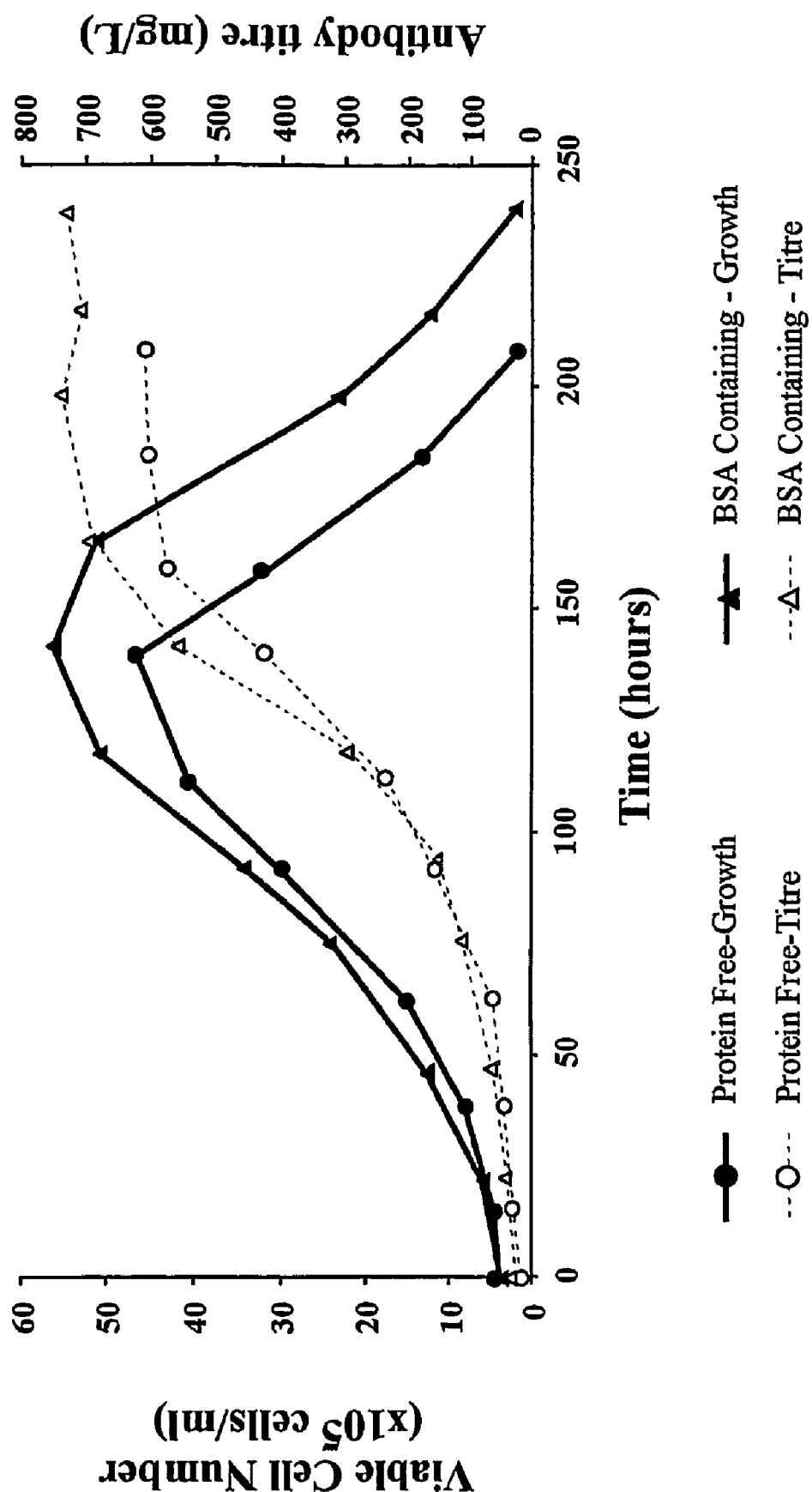
FIG. 6: illustrates the ability of ferric ammonium citrate to provide all required iron for growth of a myeloma cell line in a protein free medium and in a serum free medium under agitated suspension fermentation conditions.
Figure 7:
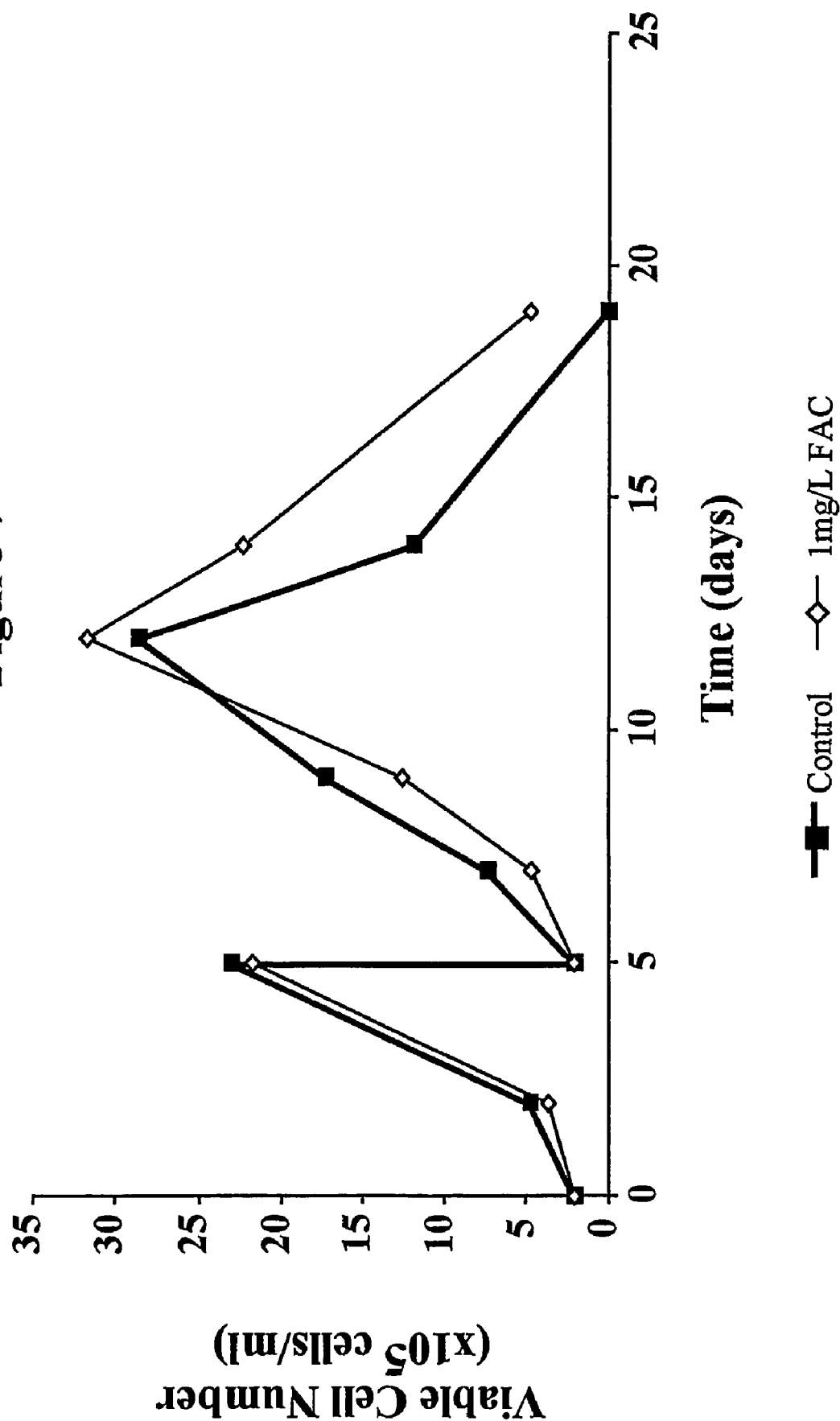
FIG. 7: illustrates that the ability of a myeloma cell line to grow with ferric ammonium citrate as the sole iron source is not due to transfection with the GS selection system.

FIG. 6 shows growth and antibody production in the two fermentations. This figure clearly shows that FAC is able to support good growth and antibody production in both media.

This result demonstrates the ability of FAC to support growth to high cell densities and production to high titres in both protein containing (i.e. serum free) and protein free medium.

Example 7

FAC in Protein Free Medium can Support Growth to High Cell Densities and Production to High Titres The following example illustrates that FAC can be used as the sole source of iron in the protein free medium of Example 6 and that this FAC supplemented medium can support growth to high cell densities and to high titres for a range of GS-NSO cell lines and at manufacturing scale.

Methods

Three GS-NSO cell lines expressing different antibodies (Cell Lines C, D and E) were revived from liquid nitrogen storage directly into the protein free, FAC containing medium of Example 6. The cultures were sub-cultured multiple times in the protein free FAC containing medium and these cultures were used to inoculate bench (4.5 L) or pilot scale fed-batch fermentations. The medium and feed used in these fed-batch fermentations was optimised to provide high antibody titres.

Cell Line C was grown at both 4.5 and 100 L scale, Cell Line D at 4.5 L scale and Cell Line E at 100 L scale.

Results

Figure 8A:
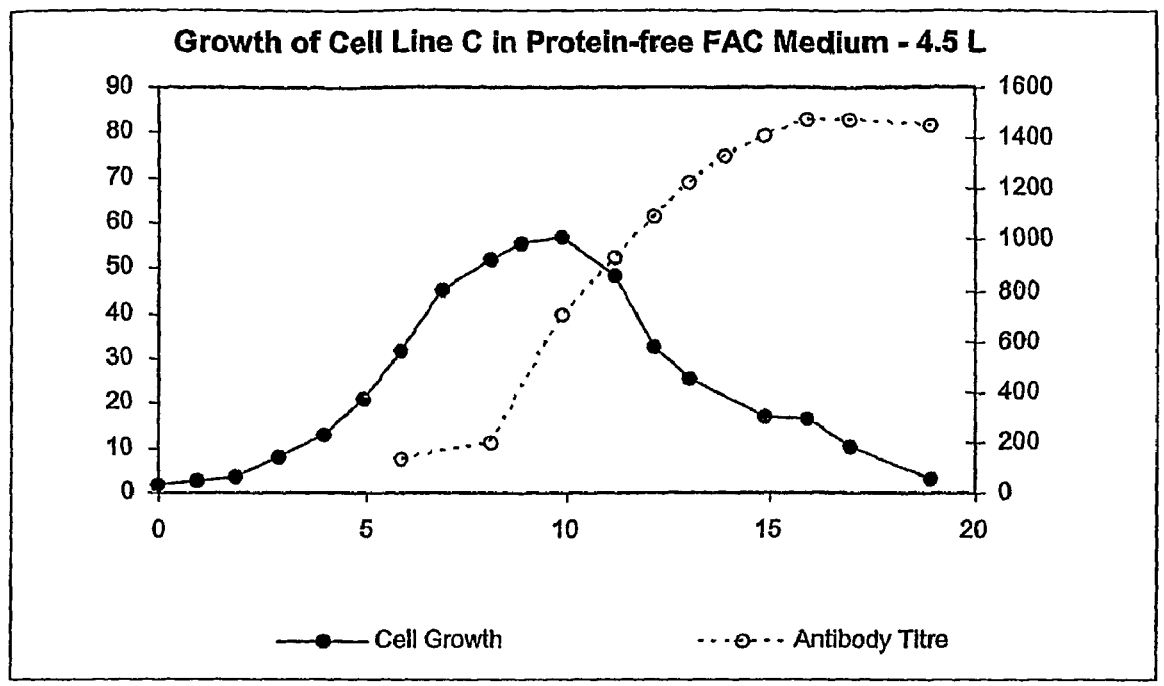
FIG. 8A: illustrates the growth of an alternative myeloma cell line in a protein free medium supplemented with ferric ammonium citrate in a bench scale fermentation.
Figure 8B:
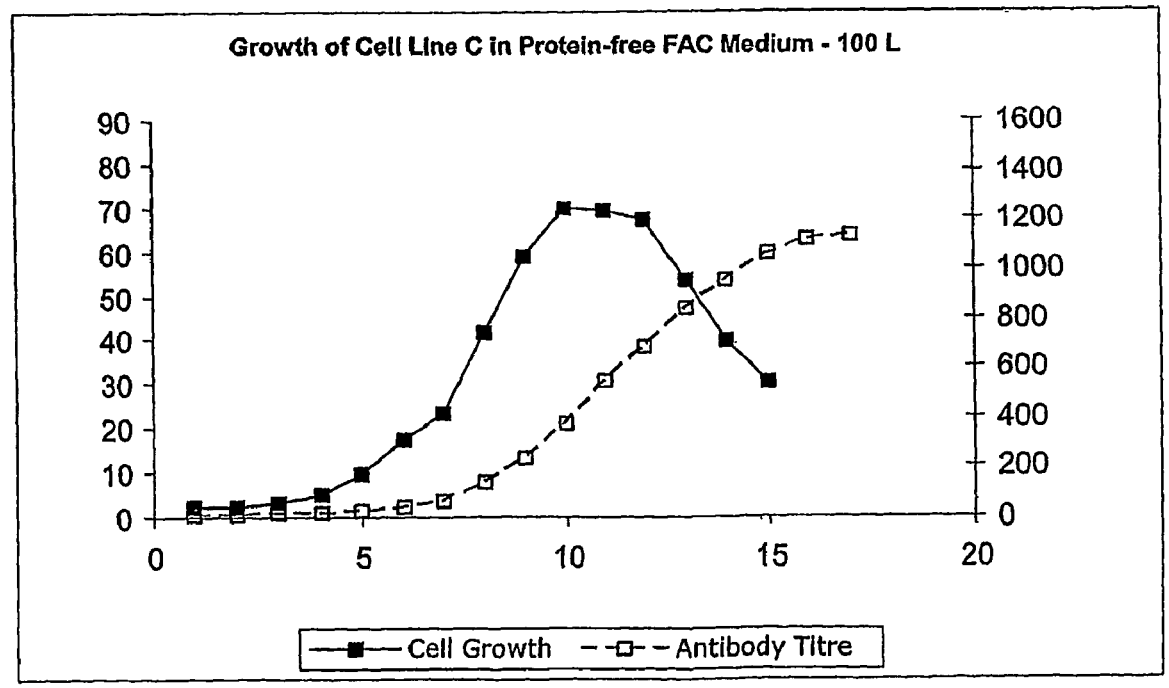
FIG. 8B: illustrates the growth of a myeloma cell line in a protein free medium supplemented with ferric ammonium citrate in a 100 L pilot scale fed-batch fermentation.
Figure 9:
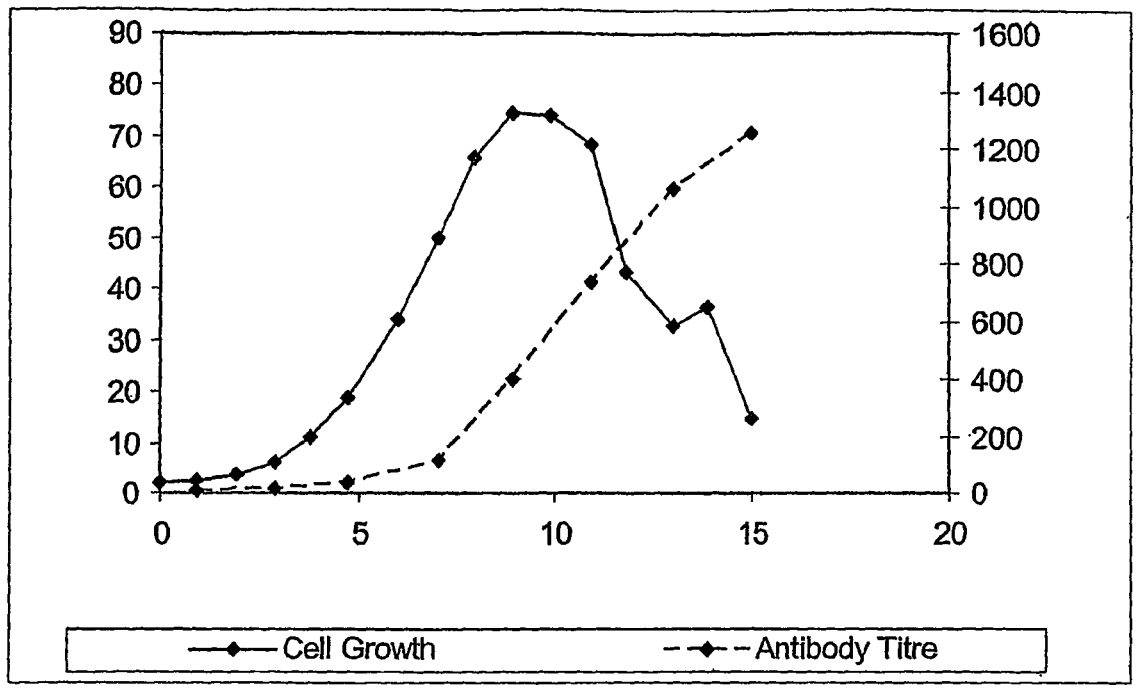
FIG. 9: illustrates the growth of a further myeloma cell line in a protein free medium supplemented with ferric ammonium citrate in a bench scale fermentation.
Figure 10:
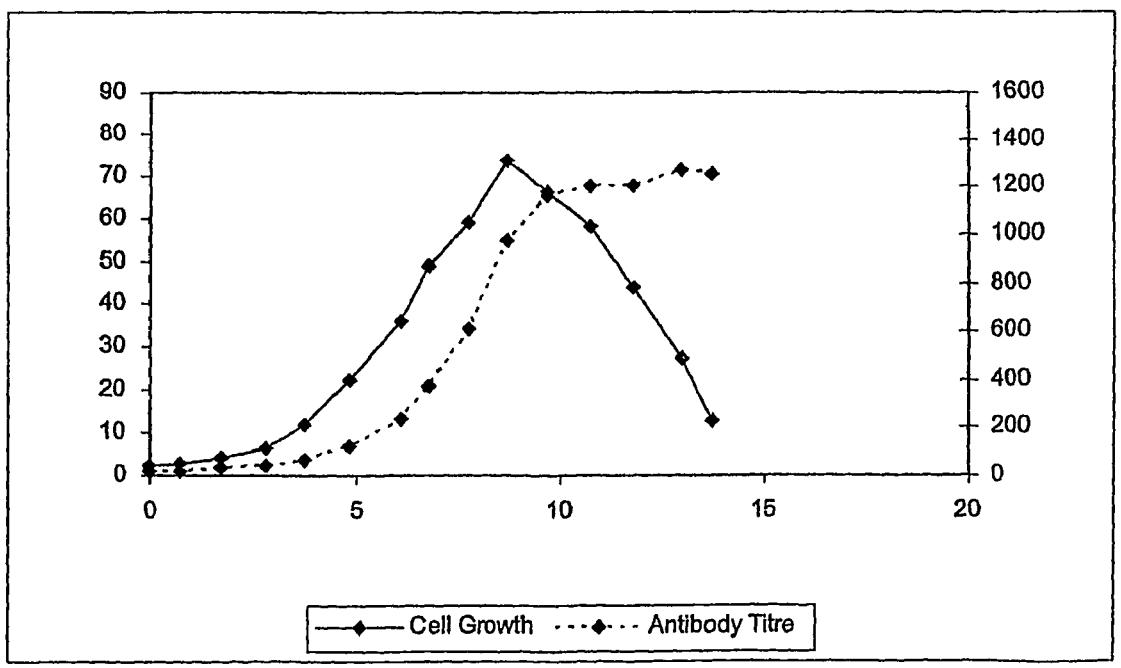
FIG. 10: illustrates the growth of a further myeloma cell line in a protein free medium supplemented with ferric ammonium citrate in a 100 L pilot scale fed-batch fermentation.

FIG. 8A shows growth and antibody production of Cell Line C in 4.5 L fermentations. FIG. 8B shows growth and antibody production of Cell Line C in 100 L fermentations. FIGS. 9 and 10 show growth and antibody production of Cell Line D in 4.5 L and Cell Line E in 100 L fermentations respectively.

These figures show clearly that protein free FAC medium supports good growth of, and antibody productivity in, a wide range of cell lines, and at manufacturing scale.

These results demonstrate the ability of FAC to support the growth and antibody production of a wide range of cell lines in a chemically-defined protein and animal component free medium. This has importance in the use of antibody for human therapeutic use as it will eliminate the risk of introducing adventitious infectious agents from animal derived compounds.

Example 8

The Ability of NS0 to Grow Using FAC as the Sole Iron Source is not Due to Transfection with the GS Selection System A recombinant NS0 mouse myeloma cell line expressing human antibodies and selected using a G418 selection system was used to assess the ability of FAC to support the growth of NS0 cells transfected with an alternative to the GS selection system.

Methods

Cells cultured in GSF serum free medium containing 1 mg/L transferrin, 0.1 mg/L FAC and 6 mM glutamine were subcultured by dilution back to $2 \times 10^5$ into fresh GSF serum free medium containing either 1 mg/L FAC, or 1 mg/L transferrin and 0.1 mg/L FAC. After 5 days, flasks were subcultured and then allowed to follow the full growth cycle. The experiment was carried out in shake flasks with sealed caps incubated in a reciprocal shaker at 36.5° C. and 125 rpm. Flasks were gassed initially and at 2 day intervals with 5% $CO_2$/95% Air.

Results

Equivalent growth was observed in both media, indicating that FAC is capable of supporting growth of NS0 cells transfected using an alternative selection system.

This result demonstrates that the ability of NS0 to grow using FAC as the sole iron source is not due to transfection with the GS selection system.

Example 9

Preparation of Modified CDSS Media

Modified CDSS was prepared as follows:

To 1 L of DMEM/F12 (1:1) (Gibco BRL. 1× liquid cat. no. 21331), agitated using a magnetic stirrer, the components below were added in the following order, taking care to ensure each was fully dissolved before addition of the next:

1 g Pluronic F-68 (Sigma P-1300)
50 nM Sodium selenite anhydrous (Sigma S-5261) (from a 25 μM stock solution)
2 μM Zinc Sulphate heptahydrate (Sigma Z-0251) (from a 2 mM stock solution)
0.5 ml Clevelands trace elements I (Cellgro 99-175)
1 ml Clevelands trace elements II (Cellgro 99-176)
20 μM Ethanolamine (Sigma E-0135)
40 ml GS supplement (JRHBiosciences 58672)
1.3 g Sodium hydrogen carbonate (BDH 102475W)
3.6 ml 2M Hydrochloric acid (BDH 190675T)
For glutamine dependant cell lines only:
0.88 g Glutamine (Sigma G-5763)
For control medium containing transferrin only:
0.1 mg Ferric ammonium citrate (BDH 271634K) (from a 1 mg/ml stock)
1 mg Human transferrin (Serologicals Proteins 82-349)

The media was allowed to mix and then filtered using a 0.2 μm membrane.

A soluble iron compound such as ferric ammonium citrate is added to the above medium from stock solutions either during preparation, i.e. concomitantly with the other ingredients, or once the medium has been prepared.

The invention claimed is:

1. A method for the in vitro culture of a myeloma cell line, said method comprising:
    (a) inoculating a culture medium with the myeloma cell line, said medium being capable of supporting the growth of said myeloma cell line and comprising iron at concentrations in the medium of from 0.064 mg/L to 1.6 mg/L, wherein said medium does not contain any of a transferrin, a lipophilic chelator, a synthetic nitrogen-containing chelator and a lipophilic synthetic nitrogen-containing chelator; and
    (b) growing of the inoculated culture medium under appropriate conditions and using agitated suspension culture, and
    wherein the source of iron is a soluble iron compound selected from the group consisting of ferric ammonium citrate, ferric ammonium oxalate, ferric ammonium fumarate, ferric ammonium malate and ferric ammonium succinate.

2. The method of claim 1 wherein the concentration of iron in the medium is from about 0.16 mg/L to about 0.32 mg/L.

3. The method of claim 1 wherein the source of iron is ferric ammonium citrate.

4. The method of claim 1 wherein the medium is serum free, protein free, free of components of animal derivation or is chemically defined.

5. The method of claim 1 wherein the myeloma cell line is selected from the group consisting of an NSO series cell line, a P3 series cell line, MOPC series cell line, the MPC-11 cell line, the J558L cell line, the K6H6/B5 cell line, the 45.6.TG1.7 cell line, the YO cell line, the Y3 HTK cell line, the RPMI 8226 cell line and the U266B1 cell line.

6. The method of claim 1 wherein the myeloma cell line is the NSO cell line.

7. A method for the in vitro culture of a myeloma cell line, the method comprising:
(a) inoculating a culture medium with the myeloma cell line, said medium being capable of supporting the growth of said myeloma cell line and comprising ferric ammonium citrate at a concentration in the medium of from 0.4 mg/L to 10 mg/L, wherein said medium does not contain any of a transferrin, a lipophilic chelator, a synthetic nitrogen-containing chelator and a lipophilic synthetic nitrogen-containing chelator; and
(b) growing of the inoculated culture medium under appropriate conditions and using agitated suspension culture.

8. The method of claim 7 wherein the ferric ammonium citrate is present in the medium at a concentration of from about 1 mg/L to about 2 mg/L.

9. A process for obtaining a mammalian cell product comprising culturing a myeloma cell capable of producing said product under agitated suspension culture and in a culture medium capable of supporting the growth of said myeloma cell line, said medium comprising iron at concentrations in the medium of from 0.064 mg/L to 1.6 mg/L, or ferric ammonium citrate at a concentration in the medium of from about 0.4 mg/L to about 10 mg/L, wherein said medium does not contain any of a transferrin, a lipophilic chelator, a synthetic nitrogen-containing chelator and a lipophilic synthetic; nitrogen-containing chelator; and recovering said mammalian cell product, and
wherein the source of iron is a soluble iron compound selected from the group consisting of ferric ammonium citrate, ferric ammonium oxalate, ferric ammonium fumarate, ferric ammonium malate and ferric ammonium succinate.

10. The process of claim 9 wherein the concentration of iron in the medium is from about 0.16 mg/L to about 0.32 mg/L.

11. The process of claim 9 wherein the source of iron is ferric ammonium citrate.

12. The process of claim 9 wherein the ferric ammonium citrate is present in the medium at a concentration of from about 1 mg/L to about 2 mg/L.

13. The process of claim 9 wherein the medium is serum free, protein free, free of components of animal derivation or is chemically defined.

14. The process of claim 9 wherein the myeloma cell line is selected from the group consisting of an NSO series cell line, a P3 series cell line, a MOPC series cell line, the MPC-11 cell line, the J558L cell line, the K6H6/B5 cell line, the 45.6.TG1.7 cell line, the YO cell line, the Y3 HTK cell line, the RPMI 8226 cell line and the U266B1 cell line.

15. The process of claim 9 wherein the myeloma cell line is the NSO cell line.

16. The process of claim 9 wherein the cell product is at least one product selected from the group consisting of a polypeptide, a protein, a hormone, a lymphokine, an interleukin, an industrially useful enzyme and a therapeutically useful enzyme.

17. The process of claim 16 wherein the cell product is an antibody or fragment thereof.

* * * * *

UNITED STATES PATENT AND TRADEMARK OFFICE
CERTIFICATE OF CORRECTION

PATENT NO. : 8,361,797 B2  
APPLICATION NO. : 10/567453  
DATED : January 29, 2013  
INVENTOR(S) : Osborne et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1020 days.

Signed and Sealed this
First Day of September, 2015

Michelle K. Lee
*Director of the United States Patent and Trademark Office*